US008244335B2

(12) United States Patent
Kumar et al.

(10) Patent No.: US 8,244,335 B2
(45) Date of Patent: Aug. 14, 2012

(54) NON-INVASIVE CARDIAC MONITOR AND METHODS OF USING CONTINUOUSLY RECORDED CARDIAC DATA

(75) Inventors: Uday N. Kumar, San Francisco, CA (US); Joseph A. Knight, Palm Harbor, FL (US); Kit Yee Au-Yeung, San Francisco, CA (US); John Warren White, San Francisco, CA (US)

(73) Assignee: The Board of Trustees of the Leland Stanford Junior University, Palo Alto, CA (US)

( * ) Notice: Subject to any disclaimer, the term of this patent is extended or adjusted under 35 U.S.C. 154(b) by 715 days.

(21) Appl. No.: 11/703,335

(22) Filed: Feb. 6, 2007

(65) Prior Publication Data

US 2007/0225611 A1 Sep. 27, 2007

Related U.S. Application Data

(60) Provisional application No. 60/765,467, filed on Feb. 6, 2006, provisional application No. 60/786,502, filed on Mar. 29, 2006.

(51) Int. Cl.
*A61B 5/0432* (2006.01)
(52) U.S. Cl. ...................................... 600/509
(58) Field of Classification Search .................. 600/507, 600/509, 513–517, 523
See application file for complete search history.

(56) References Cited

U.S. PATENT DOCUMENTS

| 3,215,136 | A |   | 11/1965 | Holter et al. |
| 3,547,107 | A |   | 12/1970 | Chapman et al. |
| 4,123,785 | A |   | 10/1978 | Cherry et al. |
| 4,274,420 | A |   | 6/1981 | Hymes |
| 4,333,475 | A | * | 6/1982 | Moreno et al. ................. 600/524 |
| 4,535,783 | A |   | 8/1985 | Marangoni |
| 4,736,752 | A |   | 4/1988 | Munck et al. |
| 4,981,141 | A | * | 1/1991 | Segalowitz .................. 600/509 |
| 5,027,824 | A |   | 7/1991 | Dougherty et al. |
| 5,086,778 | A |   | 2/1992 | Mueller et al. |
| 5,205,295 | A |   | 4/1993 | Del Mar et al. |
| 5,228,450 | A |   | 7/1993 | Sellers |
| 5,483,967 | A |   | 1/1996 | Ohtake |
| 5,489,624 | A |   | 2/1996 | Kantner et al. |
| 5,511,553 | A |   | 4/1996 | Segalowitz |

(Continued)

FOREIGN PATENT DOCUMENTS

WO  WO 01/16607 A2  3/2001

(Continued)

OTHER PUBLICATIONS

Del Mar et al.; The history of clinical holter monitoring; A.N.E.; vol. 10; No. 2; pp. 226-230; Apr. 2005.

(Continued)

*Primary Examiner* — Niketa Patel
*Assistant Examiner* — Michael D Abreu
(74) *Attorney, Agent, or Firm* — Knobbe Martens Olson & Bear LLP

(57) ABSTRACT

Embodiments of the present invention provide a method of analyzing cardiac information by collecting a plurality of self-contained, wearable, portable cardiac monitors each of the cardiac monitors electronically storing at least 24 hours of continuously detected and unanalyzed cardiac signals from a mammal. Next, retrieving cardiac information stored in each of the plurality of self-contained portable cardiac monitors. Next, forwarding retrieved cardiac information.

15 Claims, 22 Drawing Sheets

U.S. PATENT DOCUMENTS

| | | | |
|---|---|---|---|
| 5,536,768 | A | 7/1996 | Kantner et al. |
| 5,626,140 | A | 5/1997 | Feldman et al. |
| 5,634,468 | A | 6/1997 | Platt et al. |
| 5,645,068 | A | 7/1997 | Mezack et al. |
| 5,730,143 | A | 3/1998 | Schwarzberg |
| 5,749,365 | A | 5/1998 | Magill |
| 6,093,146 | A | 7/2000 | Filangeri |
| 6,102,856 | A | 8/2000 | Groff et al. |
| 6,117,077 | A | 9/2000 | Del Mar et al. |
| 6,169,915 | B1 | 1/2001 | Krumbiegel et al. |
| 6,200,265 | B1 | 3/2001 | Walsh et al. |
| 6,232,366 | B1 | 5/2001 | Wang et al. |
| 6,238,338 | B1 | 5/2001 | DeLuca et al. |
| 6,385,473 | B1 | 5/2002 | Haines et al. |
| 6,416,471 | B1* | 7/2002 | Kumar et al. ............... 600/300 |
| 6,454,708 | B1 | 9/2002 | Ferguson et al. |
| 6,456,872 | B1 | 9/2002 | Faisandier |
| 6,589,187 | B1 | 7/2003 | Dirnberger et al. |
| 6,605,046 | B1* | 8/2003 | Del Mar ..................... 600/507 |
| 6,690,959 | B2 | 2/2004 | Thompson |
| 6,701,184 | B2 | 3/2004 | Henkin |
| 6,801,802 | B2 | 10/2004 | Sitzman et al. |
| 6,881,191 | B2 | 4/2005 | Oakley et al. |
| 6,893,396 | B2 | 5/2005 | Schulze et al. |
| 6,954,163 | B2 | 10/2005 | Toumazou et al. |
| 7,072,708 | B1 | 7/2006 | Andresen et al. |
| 7,072,709 | B2 | 7/2006 | Xue |
| 7,076,283 | B2 | 7/2006 | Cho et al. |
| 7,076,287 | B2 | 7/2006 | Rowlandson |
| 7,076,288 | B2 | 7/2006 | Skinner |
| 7,076,289 | B2 | 7/2006 | Sarkar et al. |
| 7,079,977 | B2 | 7/2006 | Osorio et al. |
| 7,082,327 | B2 | 7/2006 | Houben |
| 7,193,264 | B2 | 3/2007 | Lande |
| 7,266,361 | B2 | 9/2007 | Burdett |
| 2003/0069510 | A1* | 4/2003 | Semler ....................... 600/509 |
| 2003/0083559 | A1 | 5/2003 | Thompson |
| 2004/0032957 | A1 | 2/2004 | Mansy et al. |
| 2004/0215091 | A1 | 10/2004 | Lohman et al. |
| 2005/0101875 | A1 | 5/2005 | Semler et al. |
| 2005/0165323 | A1 | 7/2005 | Montgomery et al. |
| 2005/0277841 | A1 | 12/2005 | Shennib |
| 2006/0030781 | A1 | 2/2006 | Shennib |
| 2006/0030782 | A1 | 2/2006 | Shennib |
| 2006/0047215 | A1 | 3/2006 | Newman et al. |
| 2006/0084883 | A1 | 4/2006 | Linker |
| 2006/0142648 | A1 | 6/2006 | Banet et al. |
| 2006/0142654 | A1 | 6/2006 | Rytky |
| 2006/0149156 | A1 | 7/2006 | Cochran et al. |
| 2006/0155173 | A1 | 7/2006 | Anttila et al. |
| 2006/0155183 | A1 | 7/2006 | Kroecker et al. |
| 2006/0155199 | A1 | 7/2006 | Logier et al. |
| 2006/0155200 | A1 | 7/2006 | Ng |
| 2006/0161064 | A1 | 7/2006 | Watrous et al. |
| 2006/0161065 | A1 | 7/2006 | Elion |
| 2006/0161066 | A1 | 7/2006 | Elion |
| 2006/0161067 | A1 | 7/2006 | Elion |
| 2006/0161068 | A1 | 7/2006 | Hastings et al. |
| 2006/0224072 | A1* | 10/2006 | Shennib ....................... 600/509 |
| 2006/0264767 | A1 | 11/2006 | Shennib |
| 2007/0003695 | A1 | 1/2007 | Tregub et al. |
| 2007/0249946 | A1 | 10/2007 | Kumar et al. |
| 2007/0255153 | A1 | 11/2007 | Kumar et al. |

FOREIGN PATENT DOCUMENTS

| | | |
|---|---|---|
| WO | WO 2007/049080 A1 | 3/2007 |
| WO | WO 2007/036748 A2 | 4/2007 |
| WO | WO 2007/072069 A2 | 6/2007 |

OTHER PUBLICATIONS

Enseleit et al.; Long-term continuous external electrocardiographic recording: a review; Europsace; vol. 8; pp. 255-266; 2006.

Kennedy et al.; The history, science, and innovation of holter technology; A.N.E.; vol. 11; No. 1; pp. 85-94; 2006.

Reiffel et al.; Comparison of autotriggered memory loop recorders versus standard loop recorders versus 24-hour holter monitors for arrhythmia detection; Am. J. Cardiology; vol. 95; pp. 1055-1059; May 1, 2005.

Ward et al.; Assessment of the diagnostic value of 24-hour ambulatory electrocardiographic monitoring; Biotelemetry Patient monitoring; vol. 7; 1980.

Zimetbaum et al.; The evolving role of ambulatory arrhythmia monitoring in general clinic practice; Ann. Intern. Med.; vol. 130; pp. 848-8556; 1999.

Zimetbaum et al.; Utility of patient-activated cardiac event recorders in general clinical practice; The Amer. J. of Cardiology; vol. 79; Feb. 1, 1997.

Hoefman et al.; Optimal duration of event recording for diagnosis of arrhythmias in patients with palpitations and light-headedness in the general practice; Family Practice; Dec. 7, 2006.

Ziegler et al.; Comparison of continuous versus intermittent monitoring of atrial arrhythmias; Heart Rhythm; vol. 3; No. 12; pp. 1445-1452; Dec. 2006.

* cited by examiner

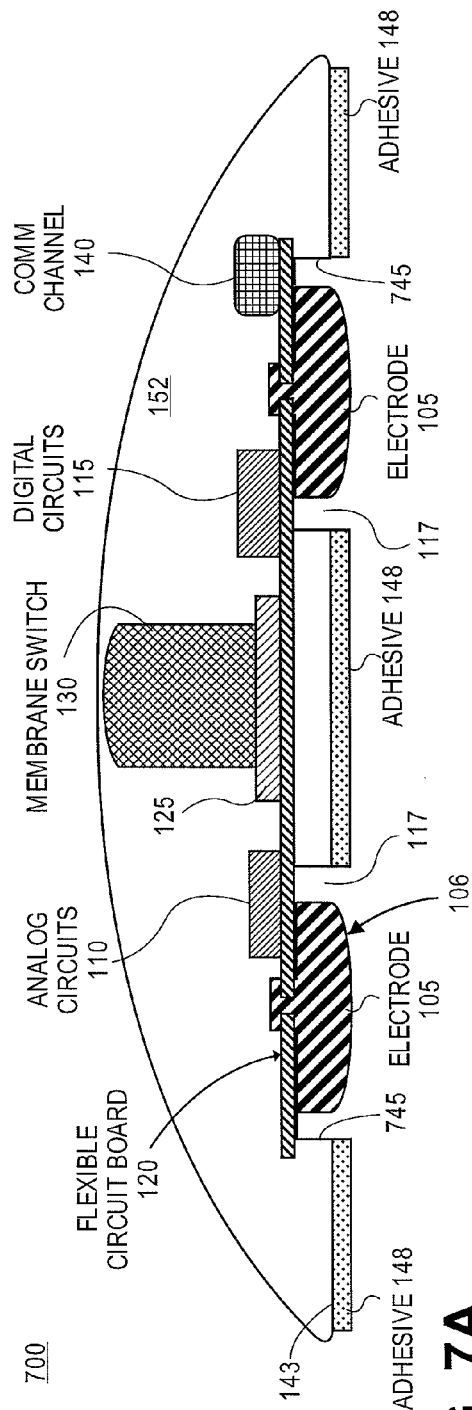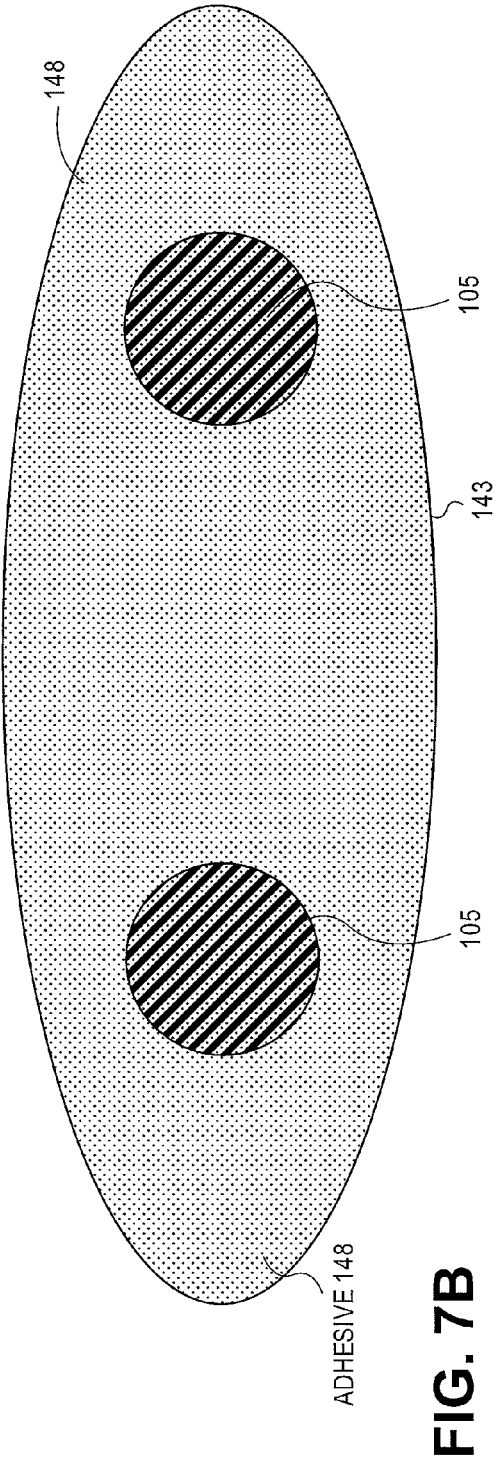
FIG. 7A
FIG. 7B

1800

```
┌─────────────────────────────────────────┐
│  ATTACHING A SELF-CONTAINED, WEARABLE,  │
│  PORTABLE CARDIAC MONITOR TO THE MAMMAL │
│  TO CREATE A CHAMBER CONTAINING         │
│  ELECTRODES USED TO DETECT CARDIAC      │
│  SIGNALS FROM THE MAMMAL                │
│                  1810                   │
└─────────────────────────────────────────┘
                    │
                    ▼
┌─────────────────────────────────────────┐
│  CONTINUOUSLY DETECTING WITHOUT         │
│  ANALYZING THE CARDIAC SIGNALS FROM THE │
│  MAMMAL FOR AT LEAST 24 HOURS           │
│                  1820                   │
└─────────────────────────────────────────┘
                    │
                    ▼
┌─────────────────────────────────────────┐
│  STORING INFORMATION RELATED TO         │
│  SUBSTANTIALLY ALL DETECTED CARDIAC     │
│  SIGNALS IN THE CARDIAC MONITOR         │
│                  1830                   │
└─────────────────────────────────────────┘
```

```
┌─────────────────────────────────────────────┐
│ COLLECTING A PLURALITY OF SELF-CONTAINED,   │
│ WEARABLE, PORTABLE CARDIAC MONITORS EACH OF │
│ THE CARDIAC MONITORS ELECTRONICALLY STORING AT │
│ LEAST 24 HOURS OF CONTINUOUSLY DETECTED AND │
│ UNANALYZED CARDIAC SIGNALS FROM A MAMMAL    │
│                   1910                       │
└─────────────────────────────────────────────┘
                      │
                      ▼
┌─────────────────────────────────────────────┐
│ RETRIEVE CARDIAC INFORMATION STORED IN      │
│ EACH OF THE PLURALITY OF SELF-CONTAINED     │
│ PORTABLE CARDIAC MONITORS                   │
│                   1920                       │
└─────────────────────────────────────────────┘
                      │
                      ▼
┌─────────────────────────────────────────────┐
│        FORWARDING RETRIEVED CARDIAC         │
│                INFORMATION                   │
│                   1930                       │
└─────────────────────────────────────────────┘
```

FIG. 19

NON-INVASIVE CARDIAC MONITOR AND METHODS OF USING CONTINUOUSLY RECORDED CARDIAC DATA

CROSS-REFERENCE TO RELATED APPLICATIONS

This application claims the benefit of U.S. Provisional Application No. 60/765,467 filed Feb. 6, 2006, titled, "Non-Invasive Cardiac Rhythm Monitor" and U.S. Provisional Application No. 60/786,502 filed Mar. 29, 2006, titled, "Non-Invasive Rhythm Monitor Business Process" each of which is incorporated herein by reference in its entirety.

BACKGROUND OF THE INVENTION

Abnormal heart rhythms, or arrhythmias, may cause various types of symptoms, such as loss of-consciousness, palpitations, dizziness, or even death. An arrhythmia that causes symptoms such as these is usually a marker of significant underlying heart disease in the conduction system. It is important to make the diagnosis that these symptoms are due to an abnormal heart rhythm since treatment with various procedures, such as pacemaker implantation or percutaneous catheter ablation, can successfully ameliorate these problems and prevent significant morbidity and mortality.

Since these symptoms can often be due to other, less serious causes, a key challenge is to determine when any of these symptoms are due to an arrhythmia. Oftentimes, arrhythmias occur infrequently and/or episodically making rapid and reliable diagnosis difficult. Currently, cardiac rhythm monitoring is primarily accomplished through the use of devices utilizing short-duration (<1 day) electrodes affixed to the chest. Wires connect the electrodes to a recording device, usually worn on a belt or at the waist. The electrodes need daily changing and the wires are cumbersome. The devices also have limited memory and recording time. Wearing the device interferes with patient movement and often precludes performing certain activities while being monitored, such as bathing. All of these limitations severely hinder the diagnostic usefulness of the device, the compliance of patients using the device and the likelihood of capturing all important information. Lack of compliance and the shortcomings of the devices often lead to the need for additional devices, follow-on monitoring or other tests to make a correct diagnosis.

Current methods to correlate symptoms with the occurrence of arrhythmias, including the use of cardiac rhythm monitoring devices such as Holter monitors and cardiac event recorders, are often not sufficient to allow an accurate diagnosis to be made. In fact, Holter monitors have been shown to not lead to a diagnosis up to 90% of the time ("Assessment of the Diagnostic Value of 24-Hour Ambulatory Electrocariographic Monitoring", by DE Ward et al. Biotelemetry Patient Monitoring, vol. 7, published in 1980).

Additionally, the medical treatment process to actually obtain a cardiac rhythm monitoring device and initiate monitoring is very complicated as illustrated in FIGS. 1 and 2. As is made clear by reviewing FIGS. 1 and 2, there are numerous steps involved in ordering, tracking, monitoring, retrieving, and analyzing the data from the device. In most cases, the patient must go to a separate office or facility to obtain the cardiac rhythm monitoring device. The difficulty posed by these factors leads to fewer patients receiving cardiac rhythm monitoring since physicians may be reluctant to go through the paperwork and burden required to initiate monitoring for a potentially lower-risk patient who presents with mild symptoms.

Once monitoring has been initiated, a large component of the process today involves a 3rd party cardiac rhythm monitoring company which is contacted, either by the patient or directly by the device, when symptoms or certain parameters set in the device are met. The screening algorithms used by devices to automatically determine if certain parameters have been met are usually simple and not very specific since the ability to process complex electrocardiogram (ECG) data is not possible in these devices due to size, cost, and a limited ability and understanding of how to process ECG signals accurately. The 3rd party monitoring company will then retrieve the data from the device over the telephone or wirelessly from the device, and will contact the patient's physician if particular parameters are met. Though this step can be useful in some instances, for the vast majority of patients it is unnecessary and only results in a physician being needlessly contacted, often in the late hours of the night. It is extremely rare for the physician to recommend that the patient go to the hospital or emergency room to be treated at the time the physician was notified.

Further, the majority of devices used today are ordered by a cardiologist or a cardiac electrophysiologist (EP), rather than the patient's primary care physician (PCP). This is of significance since the PCP is often the first physician to see the patient and make the connection that the patient's symptoms could be due to an arrhythmia. After the patient sees the PCP, the PCP will make an appointment for the patient to see a cardiologist or an EP. This appointment is usually several weeks from the initial visit with the PCP, which in itself leads to a delay in making a potential diagnosis as well as increases the likelihood that an arrhythmia episode will occur and go undiagnosed. When the patient finally sees the cardiologist or EP, a cardiac rhythm monitoring device will usually be ordered. The monitoring period can last 24-48 hours (Holter monitor) or up to a month (cardiac event monitor). Once the monitoring has been completed, the patient must return the device, which itself can be a hassle for the patient. After the data has been processed by the monitoring company or by a technician on-site at a hospital or office, a report will finally be sent to the cardiologist or EP for analysis.

In view of the shortcomings in cardiac rhythm monitoring and the processes to utilize data collected by cardiac rhythm monitoring systems, there is a need for improved non-invasive cardiac monitoring devices and methods.

SUMMARY OF THE INVENTION

In one embodiment of the present invention, there is provided a heart monitor having a housing; a surface on the housing adapted to be sealably engaged to a mammal; an adhesive on the surface that is adapted to remain affixed to the mammal for at least 7 days. There are at least two electrodes positioned to detect an ECG of the mammal while the surface is sealably engaged to the mammal; an electronic memory within the self contained and sealed housing; and wiring within the self contained and sealed housing connecting the electronic memory to the electrodes; wherein, the electronic memory is sized to store at least 24 hours of continuous ECG information. In one aspect, the same at least two electrodes are used to detect an ECG of the mammal for as long as the adhesive remains affixed to the mammal. In another aspect, the adhesive is adapted to remain affixed to the mammal for at least 7 days without skin irritation. In another aspect, the adhesive is adapted to remain affixed to the mammal for at least 2 weeks or for at least 4 weeks. In another aspect, the wiring is entirely within the self contained and sealed housing. In another alternative embodiment, there is provided a rim extending from the surface on the housing. In one alternative, a portion of each of the least two electrodes is within a portion of the surface bounded by the rim. In another aspect, the electronic memory, the wiring and the electrodes are a single, hard wired unit. In another aspect, when the adhesive is affixed to the mammal, a watertight chamber forms around the at least two electrodes. In another alternative, when the adhesive is affixed to the mammal, the rim forms a watertight chamber around the at least two electrodes. In one aspect, the surface has a tapered thickness and extends beyond the portion of the housing containing the plurality of electrodes. In another aspect, the adhesive on the surface that is adapted to remain affixed to the mammal for at least 7 days is a pressure sensitive adhesive selected from the group consisting of: polyacrylates, polyisobutylenes, and polysiloxanes. In another alternative embodiment, the housing is made of a flexible bio compatible polymer that provides a watertight enclosure for the electronic memory and wiring.

In yet another alternative, the watertight chamber comprises separate watertight enclosures around each electrode of the at least two electrodes. In another aspect, there is provided a port for electronically accessing the electronic memory and a seal is provided on the port. The seal may be formed by the housing. In another aspect, there is provided an activation or event notation button or switch formed in the housing that is accessible while the adhesive is affixed to the mammal. In one aspect, actuation of an activation or event notation button or switch increases the fidelity of the ECG information stored in the electronic memory. In another aspect, an indication of activation or event notation button or switch activation is stored in the electronic memory with contemporaneous ECG information. In yet another alternative there is provided an indicator that activates when ECG of the mammal is being detected. In another aspect, an indicator is provided that provides a continuous indication as long as ECG of the mammal is detected. In another aspect, an indicator is provided that activates when a monitoring period is completed. In another alternative, at least a portion of the housing is colored to match the skin tone of the mammal, or contain a decoration, art work, design, illustration or cartoon character to provide a custom appearance to the device.

Another embodiment of the present invention provides a cardiac monitor having a housing; a plurality of electrodes within and extending from the housing; a state machine within the housing configured to digitialize and store in memory signals from the plurality of electrodes; a sealing surface and an adhesive on the sealing surface configured to form a watertight perimeter around the plurality of electrodes when the housing is affixed to a mammal. In one aspect, the portion of each of the plurality of electrodes that is in contact with the mammal has a rounded surface. In another aspect, the sealing surface comprises a lip having a tapered thickness. In another aspect, the thinnest portion of the sealing surface is in the outer perimeter of the sealing surface. In another aspect, the thickness of the outer perimeter of the sealing surface is less than about 2 mm. In another aspect, the sealing surface is affixed to the mammal each electrode of the plurality of electrodes is contained within a separate watertight chamber. In another aspect, the sealing surface comprises a rim extending from the self contained and sealed housing. In another aspect, when the sealing surface is affixed to the mammal each electrode of the plurality of electrodes is contained within a separate watertight chamber. In another aspect, the adhesive on the sealing surface is a pressure sensitive adhesive suited to long term cardiac monitoring. In another aspect, the adhesive on the sealing surface is a pressure sensitive adhesive selected from the group consisting of: polyacrylates, polyisobutylenes, and polysiloxanes. In another aspect, the state machine within the housing is further configured to offload data stored in memory. In another aspect, the housing is made of a flexible biocompatible polymer that provides a watertight enclosure for the state machine.

In another alternative embodiment, there is provided a method of obtaining ECG information from a mammal by attaching a self-contained, wearable, portable ECG monitor to the mammal to create a chamber containing electrodes used to detect ECG signals from the mammal; a continuously detecting without analyzing the ECG signals from the mammal for at least 24 hours; and storing information related to substantially all detected ECG signals in the ECG monitor. In one aspect, the self-contained, wearable, portable ECG monitor includes: a plurality of electrodes, a power source and memory contained within a watertight housing. In another aspect, the attaching step comprises placing the electrodes on the mammal and sealing the electrodes between the housing and the mammal using an adhesive on a rim of the housing that surrounds the electrodes. In yet another aspect, there is provided a mammal perceivable indication that the ECG monitor is operating. In another aspect, the providing step is performed after the attaching step. In another aspect, the providing step is performed after the storing step.

In another aspect, the providing step is continuously performed during the continuously detecting step. In another aspect, there is provided an indication that the ECG monitor is operating after the attaching step. In another aspect, there is a step of retrieving stored information related to substantially all detected ECG signals from the monitor and analyzing the retrieved information to identify ECG events. In one aspect, the analyzing step is performed after the ECG monitor is removed from the mammal. In another aspect, removing the ECG monitor from the mammal before the retrieving step. In another aspect, the detecting and storing steps are performed without identifying ECG events in the information related to substantially all detected ECG signals. In yet another aspect, the detecting and storing steps are performed without transferring information between the housing and a device not attached to the mammal. In another aspect, the detecting and storing steps are performed without transferring information between the housing and a device not contained within the housing. In another aspect, processing information from the storing step to determine the presence of an arrhythmia. In another alternative, processing information from the storing step is performed using more than one algorithm to determine the presence of an arrhythmia. In another alternative, processing information from the storing step to evaluate the presence of an arrhythmia is performed during a selected time interval. In one aspect, the information from the storing step is processed during the same selected time interval on more than one day. In another aspect, processing information from the storing step to evaluate the presence of an arrhythmia is performed during a time interval indicated by the mammal.

In another embodiment, there is a method of analyzing ECG information that includes collecting a plurality of self-contained, wearable, portable ECG monitors each of the ECG monitors electronically storing at least 24 hours of continuously detected and unanalyzed ECG signals from a mammal; retrieving ECG information stored in each of the plurality of self-contained portable ECG monitors; and forwarding retrieved ECG information. In one aspect, there is the: step of sending the collected self-contained portable ECG monitors to a processing center before the retrieving step. In another aspect, the forwarding step includes electronically sending retrieved ECG information to a processing center. In another aspect, the method includes removing a self contained portable ECG monitor from a mammal before the collecting step. In yet another aspect, there is a step of analyzing the retrieved ECG information to identify ECG events or parameters. In one aspect, the analyzing step is done after the forwarding step. In another aspect, the mammal specific information in at least one of the plurality of self-contained, wearable, portable ECG monitors includes substantially all of the ECG information from a mammal for at least 7 days. In another aspect, the ECG information in the forwarding step includes substantially all of the ECG information from a mammal for at least 7 days. In another aspect, the forwarding step includes providing mammal specific ECG information to a physician identified in the collecting step. In another aspect, processing information from the forwarding step to determine the presence of an arrhythmia. In another aspect, processing information from the forwarding step is performed using more than one algorithm to determine the presence of an arrhythmia. In still another aspect, processing information from the forwarding step to evaluate the presence of an arrhythmia is performed during a selected time interval. In another aspect, the information from the forwarding step is processed during the same selected time interval on more than one day. In another alternative, processing information from the forwarding step to evaluate the presence of an arrhythmia is performed during a time interval indicated by the mammal. In another aspect, processing information from the forwarding step is analyzed to determine the presence of an arrhythmia. In another aspect, the method provides a user access to information from the retrieving step or the forwarding step so that the user may process the provided information using more than one algorithm to determine the presence of an arrhythmia. In another aspect, the method provides a user access to information from the retrieving step or the forwarding step so that the user may process the provided information to evaluate the presence of an arrhythmia during a selected time interval. In another aspect, the provided information is processed during the same selected time interval on more than one day. In another aspect, the method provides a user access to information from the retrieving step or the forwarding step so that the user may process the provided information to evaluate the presence of an arrhythmia during a time interval indicated by the mammal.

INCORPORATION BY REFERENCE

All publications and patent applications mentioned in this specification are herein incorporated by reference to the same extent as if each individual publication or patent application was specifically and individually indicated to be incorporated by reference.

BRIEF DESCRIPTION OF THE DRAWINGS

The novel features of the invention are set forth with particularity in the claims that follow. A better understanding of the features and advantages of the present invention will be obtained by reference to the following detailed description that sets forth illustrative embodiments, in which the principles of the invention are utilized, and the accompanying drawings of which:

FIGS. 7A-7D illustrate various views of continuous cardiac monitor embodiments having dedicated electrode pockets;

FIG. 18 illustrates an method of method of storing continuous cardiac data;

FIG. 19 illustrates a method of collecting and analyzing data from a plurality of continuous cardiac monitors.

DETAILED DESCRIPTION OF THE INVENTION

Figure 1:
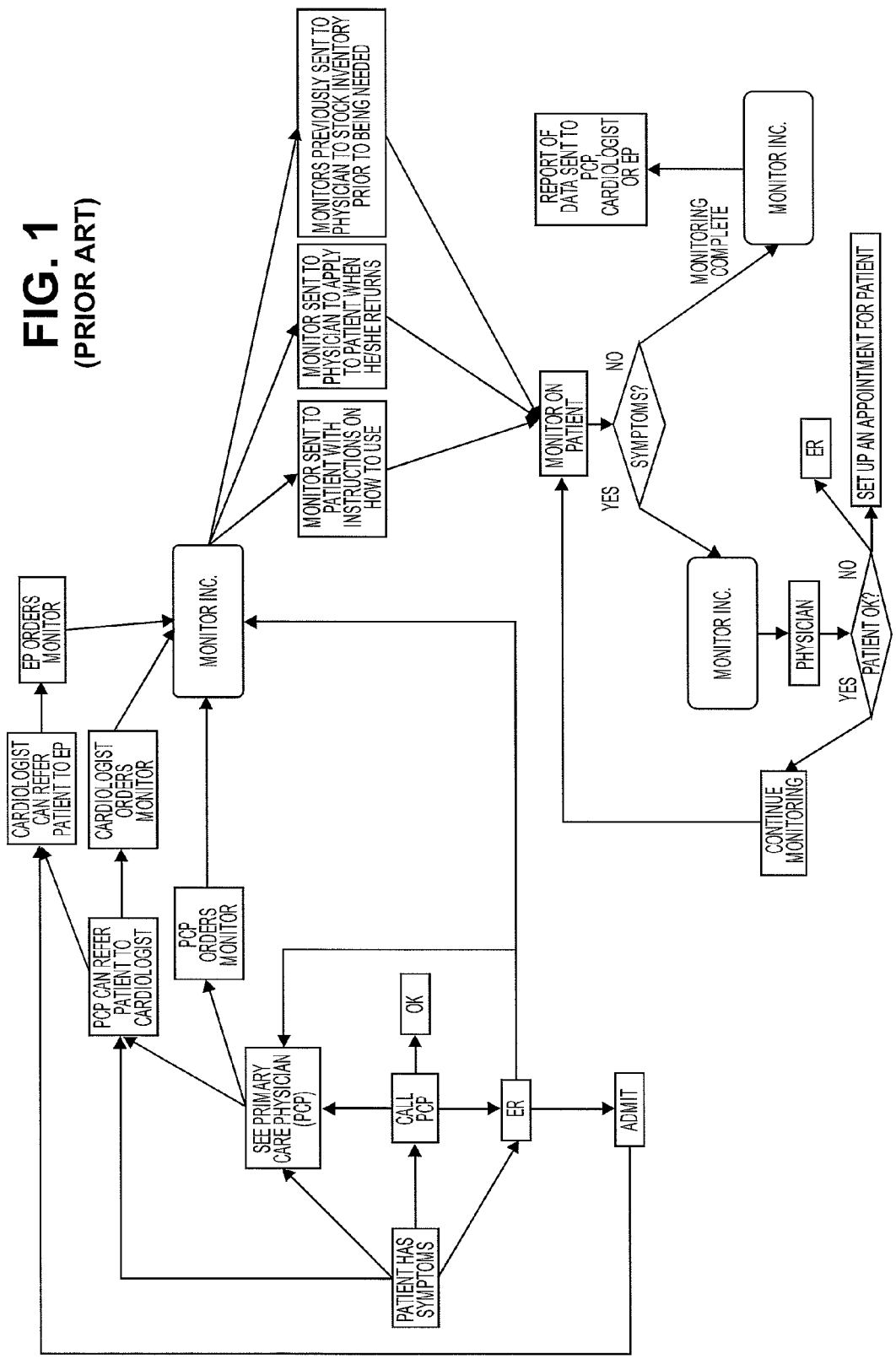
FIG. 1 is a flow chart illustrating a prior art method of cardiac monitoring.
Figure 2:
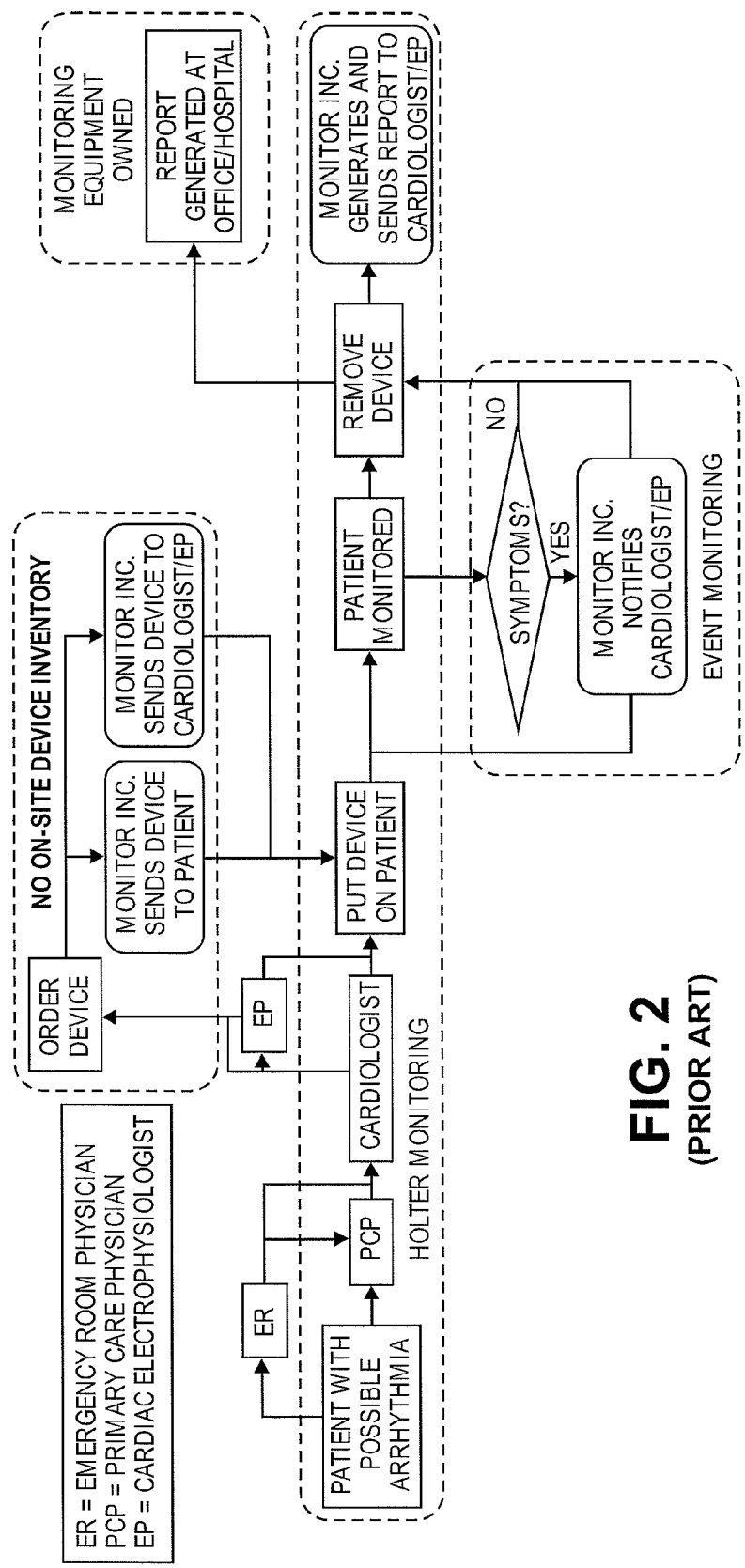
FIG. 2 is a flow chart representing a prior art method of cardiac monitoring.

In the US, over 2.3 million individuals suffer from arrhythmias, with over 700,000 new cases diagnosed annually. Over 80-90% of these arrhythmias occur in individuals over 40 due to the association of arrhythmias with aging and the occurrence of age-related events, such as heart attacks. Additionally, each year over 250,000 people die suddenly in the US due to arrhythmias ("Heart Disease and Stroke Statistics", from the American Heart Association published in 2005). Given these staggering figures, the diagnosis of arrhythmias is of crucial importance, especially since many effective treatments exist.

The occurrence of an arrhythmia can cause a range of symptoms from palpitations, dizziness, shortness-of-breath, and chest pain, to loss-of-consciousness and even death. In some individuals, arrhythmias may not lead to perceptible symptoms, even though these individuals may still be at risk for numerous arrhythmia-related complications such as strokes. Since many of the symptoms caused by arrhythmias can also be caused by other, less serious conditions, a major challenge for physicians is determining when these symptoms are actually due to an arrhythmia. This can be difficult because arrhythmias often occur infrequently and episodically, sometimes only once every few weeks and usually without warning. Additionally, arrhythmias sometimes also only last for a few seconds to a few minutes. Given that there are many types of arrhythmias, it is hard to know what treatment to recommend if an arrhythmia does not occur when a physician is present, Diagnosis is even more challenging in the patient who may be asymptomatic, but is suspected of having an arrhythmia Arrhythmias may be diagnosed using medical equipment, most often with cardiac rhythm monitors. Monitoring techniques used by available cardiac rhythm monitors include monitoring the heart rhythm for a short period of time or monitoring intermittently. Current standard techniques and devices for detecting arrhythmias include a resting ECG, which records about 15 seconds of continuous cardiac rhythm activity. Intermittent cardiac rhythm monitors include a Holter monitor that records 24-48 hours of cardiac rhythm activity during routine daily activities. The data recorded by a Holter monitor is intermittent and not actually continuous because the recorded data stream is interrupted when the patient is obligated to remove the monitor to bathe or perform other daily personal hygiene activities or to replace electrodes daily or at any other time when the electrode/monitor connection is interrupted such as when the monitor is disconnected during restless sleep. Cardiac event monitors are another form of intermittent cardiac rhythm monitor. A cardiac event monitor records cardiac activity from a looping memory only when symptoms associated with an arrhythmia are detected by the patient or by a preprogrammed arrhythmia detection algorithm in the monitor.

These diagnostic methods and tools have significant limitations in diagnosing arrhythmias and assessing the efficacy of treatment of an arrhythmia because of the limited recording time windows and the subjectivity of the activation of a monitor by a patient. If a patient is asleep and experiences an arrhythmia, then it is unlikely that the patient will wake up and activate the event monitor. Similarly, if a patient suffers from an arrhythmia outside of the parameters of the preprogrammed detection circuit, then those arrhythmias will remain undetected as well. More importantly, because these conventional intermittent cardiac rhythm monitors rely on looping memory, relevant information about the cardiac rhythm that are patient-specific or outside of the parameters of the arrhythmia detection algorithm are usually not recorded. Lack of relevant data or a more robust set of patient specific data adversely impacts the usefulness of the data acquired during a given monitoring period.

It is believed that conventional cardiac rhythm monitoring techniques hinder the ability to accurately diagnose arrhythmias because of the lack of availability of continuous patient specific data for later analysis, comparison and confirmation and the fact that the only data available for later analysis is data that has been subjectively limited during the monitoring period. In 1997, 729 consecutive cases were analyzed to test the hypothesis that continuous loop cardiac event monitors provide useful diagnostic information about common clinical problems. The study found cardiac event recorders provided an explanation of cardiac symptoms in about half the studied cases. Serious and potentially life threatening arrhythmias (ventricular tachycardia, supraventricular tachyarrhythmias (SVT) including atrial fibrillation and/or flutter or paroxysmal SVT, or high grade bradyarrhythmias) were detected in only about 25% of the cases. Importantly, the study concluded that cardiac event recorders were of little utility in identifying a probable cause of syncope and had no diagnostic yield in patients with nonspecific symptoms ("Utility of Patient-Activated Cardiac Event Recorders in General Clinical Practice", by Peter Zimetbaum et al in The American Journal of Cardiology, vol. 79, published on Feb. 1, 1997). Another study concluded that intermittent and symptom-based monitoring is highly inaccurate for identifying patients with any or long-duration atrial fibrillation or atrial tachycardia or for assessing atrial fibrillation or atrial tachycardia burden ("Comparison of continuous versus intermittent monitoring of atrial arrhythmias", by Paul Ziegler et al in Heart Rhythm, vol. 3, published in December 2006). Another 2006 study of the optimal duration of cardiac event recording found that more relevant arrhythmias (i.e., paroxysmal atrial fibrillation, atrial flutter, atrial tachycardia, SVT not specified and ventricular tachycardia) and less relevant arrhythmias (i.e., ventricular or atrial premature beats, sinus tachycardia. or bradycardia) were identified during the third week of monitoring rather than during the first two weeks of monitoring. The study concluded that a minimum of two weeks of recording appeared necessary ("Optimal duration of event recording for diagnosis of arrhythmias in patients with palpitations and light-headedness in the general practice", by Emmy Hoefman et al in Family Practice, published Dec. 7, 2006).

Since intermittent cardiac rhythm monitors record only selected moments during a monitoring period, there are large time gaps and discontinuity in the recorded data. Because of the gaps in data, time stamps in the recorded data stream are needed. The time stamps in the recorded data stream are needed to distinguish between recorded events. In some intermittent cardiac rhythm monitors, one recording is typically 4 to 5 minutes long, with about half that being used to store the time just prior to the onset of an event, and half used to store 2 to 2.5 minutes afterwards. Significantly, what is recorded, and when the recording begins, is not decided by a skilled physician but rather by the patient or auto-triggered by an arrhythmia detection algorithm. Moreover, after this 5 minute recording, there are often large indeterminate time gaps, hours or even weeks, before the recording of the next 5 minute interval is triggered by the patient or auto-triggered by an arrhythmia detection algorithm. In summary, recorded data streams in intermittent cardiac rhythm monitors consist of small blocks of time stamped ECG data separated by large time blocks where no data recordings are collected.

Rather than subjectively limit the data collected by an event monitor, embodiments of the cardiac monitor of the present invention collect substantially all cardiac or other physiological data during the monitoring period. Moreover, the monitoring period used by the present invention is longer so as to increase the likelihood that the collected continuous data will yield—an accurate diagnosis when later analyzed and evaluated. Data obtained from intermittent cardiac rhythm monitors necessarily excludes subjectively normal cardiac data. Subjectively normal data is excluded in these systems since the looping memory only records when the wearer or the monitor's detection algorithm believes that an abnormal rhythm is present. As a result, other indicia or precursors of arrhythmia outside the perception of the patient or the parameters of the monitor's arrhythmia algorithm are (1) not evaluated; (2) not recorded and (3) not available for different or more sophisticated analysis or processing.

Under-detection and under-recognition of arrhythmias in patients may have significant clinical consequences. If an arrhythmia is not detected and if it recurs, a patient is exposed to serious morbidity since arrhythmias can cause loss-of-consciousness, strokes, or heart attacks. In their most serious form, arrhythmias may lead to death. On a more practical level, the under-detection of an arrhythmia may also lead a physician caring for a patient to not treat a patient with the appropriate medications and/or procedures, which otherwise could prevent further arrhythmia episodes. Each of these consequences may be determined, evaluated or predicted using vastly different indications, symptoms, or predictors. It is highly unlikely that any single evaluation, processing or analytical technique—whether manual or automatic—will successfully determine each of the myriad of different indications, symptoms, or predictors. Rather than risk misidentifying, mischaracterizing or under-identifying an arrhythmia by choosing a preset algorithm, the continuous, unprocessed data collected by embodiments of the device described herein would provide cardiac data that may be evaluated using numerous different automatic and/or manual detection techniques during numerous temporal situations to provide a more robust and complete likelihood of diagnosis.

Rather than attempting to decide whether a rhythm is abnormal in real time by some predetermined algorithm, the continuous cardiac monitor of the invention simply creates a continuously digitized time stream over the monitoring period. The continuous cardiac monitor data storage differs from intermittent cardiac rhythm monitoring device data storage in at least at least three ways.

First, the data stored in a continuous cardiac monitor does not have the "off period" or time blanks present in intermittent cardiac rhythm monitor device data. Because the continuous monitoring electrodes are in constant skin contact during the monitoring period and the same electrodes are used during the entire monitoring period, the inventive device is on and always sensing during the monitoring period. Unlike Holter type monitors where data collection is interrupted for daily electrode changes or personal hygiene, the design of continuous cardiac monitors utilizes the same electrodes for the entire monitoring period within a sealed watertight enclosure that allows monitoring to continue regardless of the performance of personal hygiene or any other activity. Unlike loop or event type intermittent monitors, continuous cardiac monitors store all data continuously instead of over-writing temporary data when triggered to store the data. Since all rhythms are recorded during a monitoring period, there are no time gaps or intentional blanks where ECG rhythm is excluded from recording.

Second, the data stored in continuous cardiac monitors of the invention is unfiltered, unaltered, and not subjected to local or on-device processing. Continuous cardiac monitor data is simply digitized and stored. In summary, the data collected by the inventive continuous cardiac monitors described herein represents a comprehensive and complete, uninterrupted recording of a patient's cardiac data during the time of attachment and throughout the monitoring period. The data is in its natural, biological form and is not filtered by any circuit or software prior to onboard storage. Continuous cardiac monitors of the invention deliver unprocessed physiological data from the memory, upstream to a report generating computer. The complete, unfiltered data from the monitoring period may then be analyzed, processed or evaluated by a physician or other user who determines the appropriate screening, processing or evaluating algorithm or data analysis method.

In contrast, conventional intermittent cardiac rhythm monitors include hardware and software based capabilities to perform real time analog and/or digital signal processing of the selected subset of monitored data. The signal processing of these devices is needed for a variety of tasks, such as to narrow the frequency band, detect the R-wave, measure R-R intervals, and perform a myriad of tests on and around the QRS complex. The signal processing programs and microprocessor power required for such devices is large given that these devices attempt to process real time ECG data to identify ECG abnormalities based on the pre-programmed and predetermined criteria. Importantly, the kind of processing performed in intermittent cardiac rhythm monitors requires transformation of the data stream. This type of data transformation impacts what is ultimately recorded in the memory of the intermittent cardiac rhythm monitor. In addition, performing data transformations and tests locally on the device requires a filtering and detecting system, along with extensive software algorithms. However, even though a significant amount of rhythm data is never recorded, the tests performed in intermittent cardiac rhythm monitors are redundant since the selected, recorded data from these devices is provided upstream to and processed by a report generating computer.

Third, the underlying principle that determines which data gets stored and how this data is processed is different. In a continuous cardiac monitor, all data is stored irrespective of whether or not the data corresponds to an arrhythmic condition. Data is processed at the conclusion of the monitoring period using virtually any available processing algorithm or technique. If a continuous cardiac monitor device is recording, it is recording all or substantially all cardiac data.

Rather than record a continuous, unfiltered, electrical history for the monitoring period, conventional intermittent cardiac rhythm monitors make an error prone attempt at recording only the actual arrhythmia events based on either patient initiated or algorithmic auto-triggers. Since conventional rhythm monitors only seek to record perceived arrhythmia events, all other events, including unperceived arrhythmia events are excluded from the data. Conventional intermittent cardiac rhythm monitors depend upon a patient and/or an algorithm to choose what subset of data from a monitoring period will be stored and available for later review and diagnosis. As a result, data stored in the memory of such devices has a much different content. Even during recording, the data may not be all data during that period but rather only a filtered or pre-processed version of the actual data. The data is different from continuous data because of the common practice in prior art intermittent cardiac rhythm monitors to attempt to minimize the amount of data to increase the number of discrete events that can be recorded. Data is minimized using well known prior art data reduction algorithms, such as turning point algorithms, AZTEC (Amplitude Zone Time Epoch Coding), CORTES (Coordinate Reduction Time Encoding System), the data reduction algorithms and arrhythmia detection algorithms of Tompkins and Webster of the University of Wisconsin, Madison, and those found in their text, Design of Micro-Computer based Medical Instrumentation (Prentice Hall, 1981). Intermittent cardiac rhythm monitors process data concurrent with the monitoring period using only processing algorithms stored on the monitor in an attempt to record only abnormal events. If an intermittent cardiac rhythm monitoring device is on, it may or may not be recording ECG data depending upon whether an abnormal event is perceived by the patient or the on-board algorithm.

Assessing a patient's condition based on an evaluation of continuous, unprocessed, long-term cardiac data made available by the present invention has several distinct advantages. A conventional pre-set monitoring program would likely eliminate data as being outside of the pre-set parameters whereas the eliminated (i.e., not recorded) data may prove relevant only after later, more robust analysis using a different algorithm or processing technique. Since devices of the present invention record all physiologic data, a physician, or technician may process or analyze the data using any specific time during a monitoring period, any continuous time period during the monitoring period or repeatably obtaining data from a specific time period at a designated time interval. Moreover, because substantially all cardiac data is available for the entire monitoring period, the likelihood is increased that when potentially contributory events such as particular activities or situations are identified, data will be available from that identified time period as well as from nearby time periods since this data may provide clues as to why the event occurred. Conventionally recorded cardiac rhythm data does not provide such robust time based selectivity because the recorded data contains only the data that needed to be recorded based on pre-set parameters—i.e., the data included what the pre-programmed algorithm determined was an abnormal rhythm based on the specific parameters of that specific device.

Conventional intermittent cardiac rhythm monitors include processor intensive algorithms or methods processed on-chip or on-board the instrument. The inventive continuous cardiac monitors described herein are a distinct departure from prior art intermittent cardiac rhythm monitors such as, for example, the type described in US Patent Application Publication US 2003/0083559 to Thompson. The Thompson device, like other auto-trigger intermittent cardiac rhythm monitors, includes some form of a trigger and/or arrhythmia detector capability to detect and record only suspected abnormal rhythms. As a result, the Thompson device, like other auto-trigger intermittent cardiac rhythm monitors, must process and convert the incoming QRS data stream so that it may be in a form acceptable to the trigger and/or arrhythmia detector circuit(s).

The inventors of the present invention recognized that for most situations recorded cardiac monitor data—whether from an intermittent or a continuous cardiac rhythm monitor—is best processed after the monitoring period using more powerful computers and a greater variety of processing algorithms than are available on intermittent cardiac rhythm monitors. The inventors also recognized that conventional cardiac rhythm monitors include signal processing that is replicated upstream in more sophisticated systems. Embodiments of the continuous cardiac monitor of the present invention are designed contrary to intermittent cardiac rhythm monitors. As a result, instead of attempting to identify arrhythmias or process the QRS complex, continuous cardiac monitors of the invention eliminate this data processing redundancy and instead capture and record raw data for later upstream data processing using appropriate user selected processing. A continuous cardiac monitor is a biological analog signal acquisition and disposition device. Because the operation of the inventive monitoring device is built around a simple load-store-forward architecture, storage of signals in these devices requires no analog or digital signal processing. As a result, the inventive continuous cardiac monitoring device is constructed using a few common electronic components including a state machine having simple hardwired logic to perform functions related to continuous cardiac monitoring.

Recognizing that data transformation, filtering, processing, analyzing and algorithm selection are better left to individual users to analyze based on patient specific criteria after data collection, embodiments of the present invention instead record continuously all or substantially all of the data during a monitoring period. This fundamental difference results in the reduction or complete elimination of hardware and software complexity in continuous cardiac monitors. Digital signal processing components and arrhythmia detection algorithms, along with the micro-computers or microcontrollers needed to run them—so pervasive in intermittent cardiac rhythm monitors—are not needed in continuous cardiac monitors.

Figure 3A:
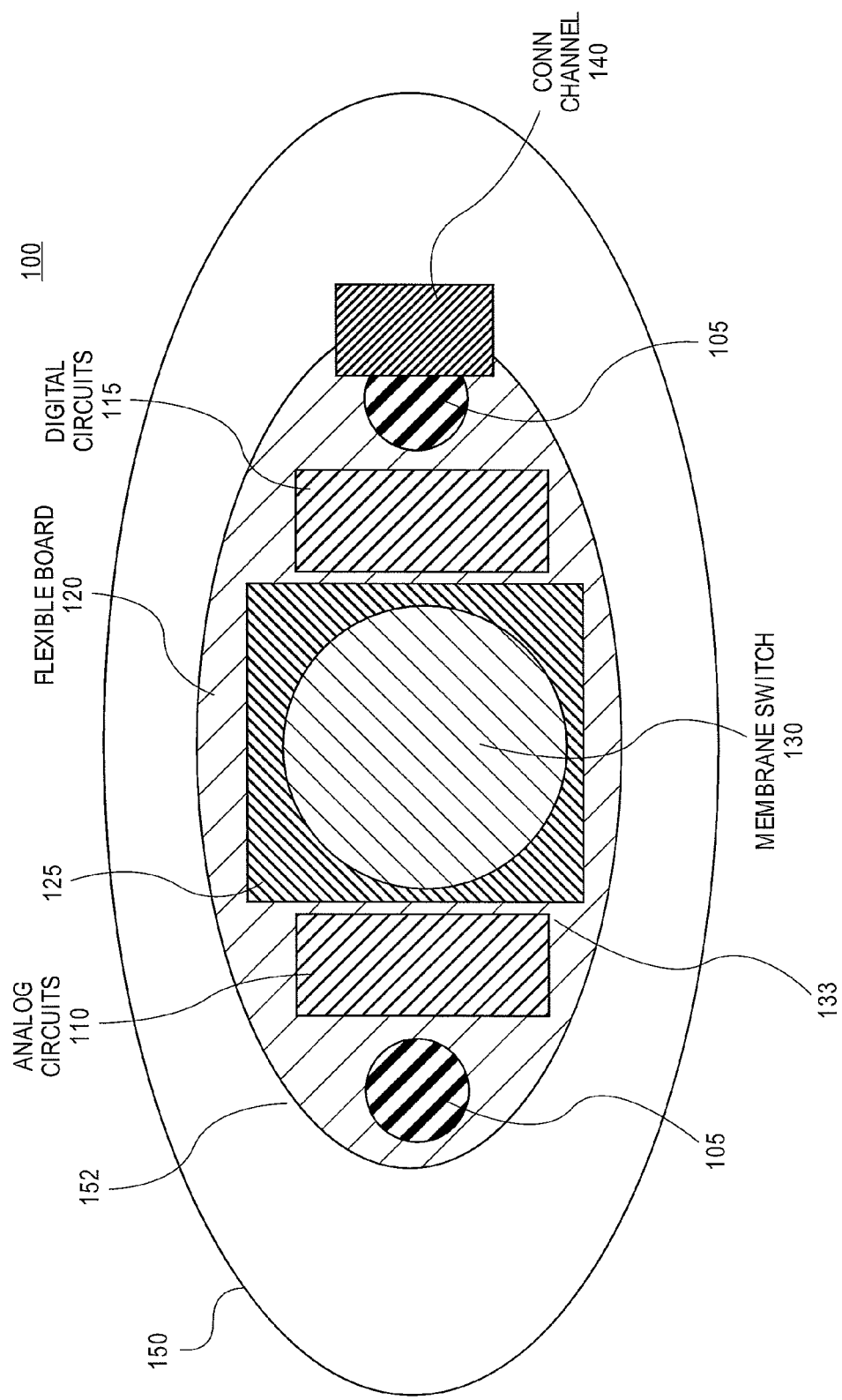
FIG. 3A is a top down view of an embodiment of a continuous cardiac monitor.

FIG. 3A illustrates a top view of an embodiment of a continuous cardiac monitor 100 according to one embodiment of the present invention. The continuous cardiac monitor 100 includes a housing 152. The housing 152 provides a watertight enclosure to encapsulate the electronic components of the device. The housing 152 may be formed from any flexible, durable material. In one embodiment, the housing is a biocompatible polymer. In one specific embodiment, the housing is formed from silicone.

The housing 152 has a central portion 133 containing the various electronic components used to record continuous physiological signals from a mammal wearing device. In the illustrated embodiment, a flexible rim or membrane 150 is a part of the housing 152 that extends beyond the footprint of the electrodes 105 and the central portion 133.

The continuous cardiac monitor 100 includes at least two electrodes 105 positioned to detect an ECG of the mammal while the surface is sealably engaged to the mammal. Contained within the self contained and sealed housing 152 are conventional electronic components such as analog circuits 110, digital circuits 115, a battery 125, memory 122 (not shown but within the digital circuits 115), an activation or event notation button or switch 130 and communications port 140 mounted on a flexible circuit board 120.

Wiring or other suitable electrical connections within the housing 152 connect the electronic memory 122 (not shown but within the digital circuits 115) to the electrodes 105. The flexible circuit board or substrate 120 may comprise a resilient material upon which several or all of the electronic and electrical components are mounted. Flexible substrate 120 may include an integral or separate interconnect pattern of electrical conductors that provide for interconnection between the various components disposed on flexible substrate 120. Suitable materials that may be used to fabricate the flexible substrate 120 include Mylar, flexible foil, Kapton, and polymer thick film (PTF).

Figure 3B:
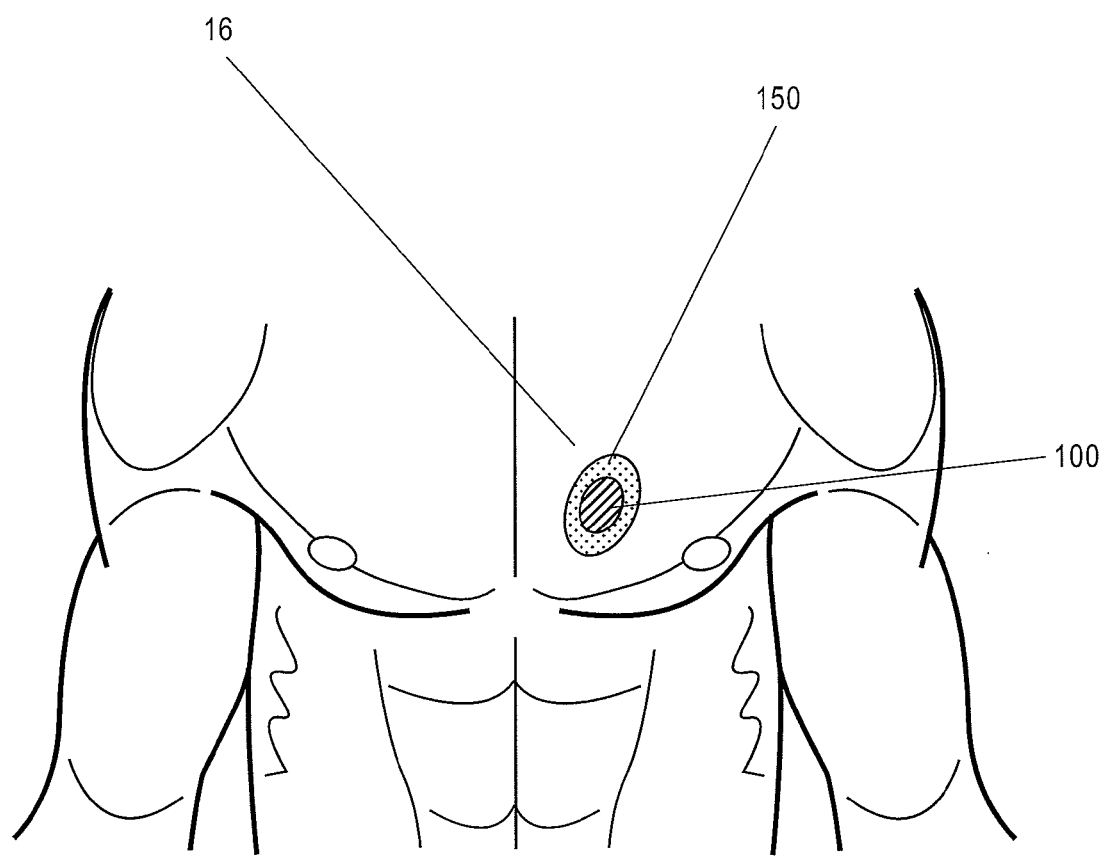
FIG. 3B illustrates the cardiac monitor of FIG. 3A affixed to the chest.

FIG. 3B illustrates a cardiac monitor 100 on the chest 16 of a male, human. The flexible membrane 150 is clearly shown extending from the central electronics portion of the device. The flexible membrane or lip 150 includes a surface adapted to be sealably engaged to a mammal. In one embodiment, there is an adhesive on the surface that is adapted to remain affixed to the mammal for at least 7 days.

As described in greater detail below, the signal detected by the electrodes 105 is continuously stored in the electronic memory 122 contained within the self contained and sealed housing 152.

The adhesives used with embodiments of the present invention are selected for long term adhesion. Long term adhesives refers to adhesives suited to maintaining a continuous cardiac monitor affixed to a mammal for the duration of the monitoring period with minimal discomfort for the mammal undergoing monitoring.

Adhesives typically used for conventional intermittent ECG electrode attachment are inadequate since these adhesives are generally intended to keep an electrode in place for only 24 hours, or perhaps 48 hours in an extreme case. Moreover, a gel component that may also act as an adhesive is commonly used in these electrodes which can be caustic to the skin if used for long-term applications such as those described herein.

We have found that certain types of adhesives, known as pressure-sensitive adhesives, or PSAs, are suited to our long-term cardiac monitoring applications. In particular, we have identified several PSA formulations, such as polyacrylates, polyisobutylenes, and polysiloxanes, suited to our applications. Hydrophilic PSAs of the general polyethylene oxide type, such as those described in U.S. Pat. No. 5,489,624 and U.S. Pat. No. 5,536,768, both to Kantner, et al., are described as being suited to the short term electrode placement typical of intermittent cardiac monitors. Specifically, Kantner describes hydrophilic polyethylene oxide PSAs used in conjunction with the short-term electrodes mentioned above and including the caustic conductive gel often found in these type of short-term disposable electrodes. As such, PSAs of this type would not likely be suited to long term monitoring applications as described herein.

We tested various polyacrylates, polyisobutylenes, and polysiloxanes PSAs on human skin to determine the long-term adhesive capabilities of these PSAs. One PSA that worked well was Duro-Tak 387-2287/87-2287—an acrylate-vinylacetate non-curing PSA available from National Starch & Chemical Co. This PSA was used to affix a prototype device similar to the device illustrated in FIG. 3A to human skin on the chest near the heart as illustrated in FIG. 3B. Our test showed that with this PSA adhesive the device remained attached in the same place on the chest skin for over 3 weeks. The subject wearing the patch performed normal daily activities such as bathing, showering, exercising, and sleeping without impediment from the device. The device was removed at the end of the test period without difficulty. An inspection of the skin after removal showed no signs of significant skin irritation or necrosis. Thus, it is believed that PSAs such as polyacrylate, polyisobutylene, or polysiloxane and the like are suited for long-term monitoring applications coextensive with the available memory on the continuous monitoring device. As such, long term monitoring devices of the present invention enable the collection of continuous long term cardiac data for a clinically relevant time period, thereby increasing the likelihood of the detection of arrhythmias. Because the continuous monitoring devices of the invention have been designed for long term monitoring, physicians and other health care providers or even individuals would have a device that may remain comfortably affixed in a monitoring condition for a wide variety of monitoring durations such one, two, three or four weeks or any number of days up to 30 days.

In addition to selecting a suitable long term adhesive, other aspects of continuous cardiac monitors of the present invention are designed to enhance patient comfort while maintaining the device in position to detect a quality signal. One aspect related to maintaining the device in position is the type of adhesive and the surface area on the device available for or dedicated to affixing the device to the skin of the mammal. During long-term applications, device/adhesive combination and the device/skin interface will be exposed to varying moisture, pressure, force, and heat conditions. It is believed that a large ratio of adhesion surface area (i.e., portion of the device available for or used to affix the device to the skin) to non-adhesion area (i.e., portion of the device not used to affix the device to skin) is useful in maintaining the device in position. Given that a mammal's body bends and is curved, we have found that by providing an area around the edges of the electronics portions of the device to increase the surface area available for adhesion also increases the likelihood that the device will remain in place during the monitoring period. Large and tapered rims as described herein dramatically increase the surface area available for adhesion. Moreover, these rims are relatively thin and flexible thereby increasing the likelihood that the device will conform to the body during movement while maintaining an adequate seal to a curved, moving, and bending surface. It is believed that providing a rim or lip to increase the surface area for adhesion is likely to be a key factor for long-term device placement.

In some embodiments, the lip is thin and flexible with a thickness that tapers away from the electronics portion of the device. Typically, the combination of the lip and the adhesive is about 1 mm to about 4 mm thick near the electronic components. The thickness near the electrical components tapers to a thickness of about 0.5 mm to about 2 mm at the outermost edge. The thin conformal nature of this tapered design decreases the likelihood that the monitor may inadvertently get caught on an article of clothing or other object or be accidentally dislodged or pulled off. Also, the adhesive lip and/or rim design also provide a watertight seal around the electrodes. This seal ensures that electrode operation and electrical integrity of the device are maintained while allowing the wearer the ability to carry on with daily activities. The slightly protruding, dome shaped electrodes described herein are pressed gently against the skin because of the enhanced adhesion qualities of the device.

The electronic memory 122 may be any conventional low power non-volatile, serial or parallel access memory with sufficient capacity to hold 0.5 Gbytes of data or more depending upon the intended duration of the continuous monitoring period and the intended the fidelity of the recorded signal. Increasing monitoring duration and/or recording fidelity will increase the amount of storage capacity needed as described in greater detail below. In one embodiment, memory 122 could also be a polymer ferroelectric memory such as, for example, the kinds of memory described in US patent application 20070003695, dated Jan. 4, 2007 by Alexander Tregub, et al., incorporated herein by reference in its entirety. The size of memory in a continuous cardiac monitor corresponds, for example, to an amount of memory sufficient to record continuous ECG data from a mammal for the intended monitoring period, or the expected duration of the monitor remaining affixed to the mammal based on the type of long term adhesive selected.

Each continuous cardiac monitor may be provided with a unique identifier such as a serial number or patient information so that when the monitor is received for processing as described below, the recorded continuous cardiac data is provided to the correct patient or patient's physician. Since each monitor may be uniquely identified, a physician or user initiating continuous monitoring may report the patient name, physician, date and time monitoring initiated into a computer and/or internet based monitoring system used to analyze continuously recorded data and generate reports. Specific portions of the data may be obtained by beginning at time of initiation of monitoring and projecting forward. The clock counter 114 tracks relative time from when the device is placed on a patient and the initiation of monitoring recorded. In embodiments having the touch sensors 119 associated with the electrodes 105, the touch sensors 119 complete the monitoring circuit and continuous recording begins. In another embodiment, time of activation is confirmed by having the user activate the event notation button 130 at a designated time on the first day of monitoring. For example, if the predetermined time is 5 pm, then on the first day of monitoring the patient will depress the button or activate the event monitor at 5 pm. When the device is later retrieved for processing and evaluation, the date of initiation is known and, by using the 5 pm event notation on the first day, all subsequent readings from 5 pm may be accurately correlated for the remainder of the monitoring period.

Alternatively, the touch sensors 119 may be logically tied with an AND function to the button 130 and input switch 136. In this example, both the touch sensors 119 and the input switch 136 must provide a signal in order for the action sequencer 160 to begin recording continuous ECG signals. Once monitoring begins, the system will have millisecond accuracy because of the clock generator and the continuous nature of the data stream. As such, the time of application is known (i.e., recorded at the doctor's office), and the device records linearly for a fixed number of days afterward.

Figure 4:
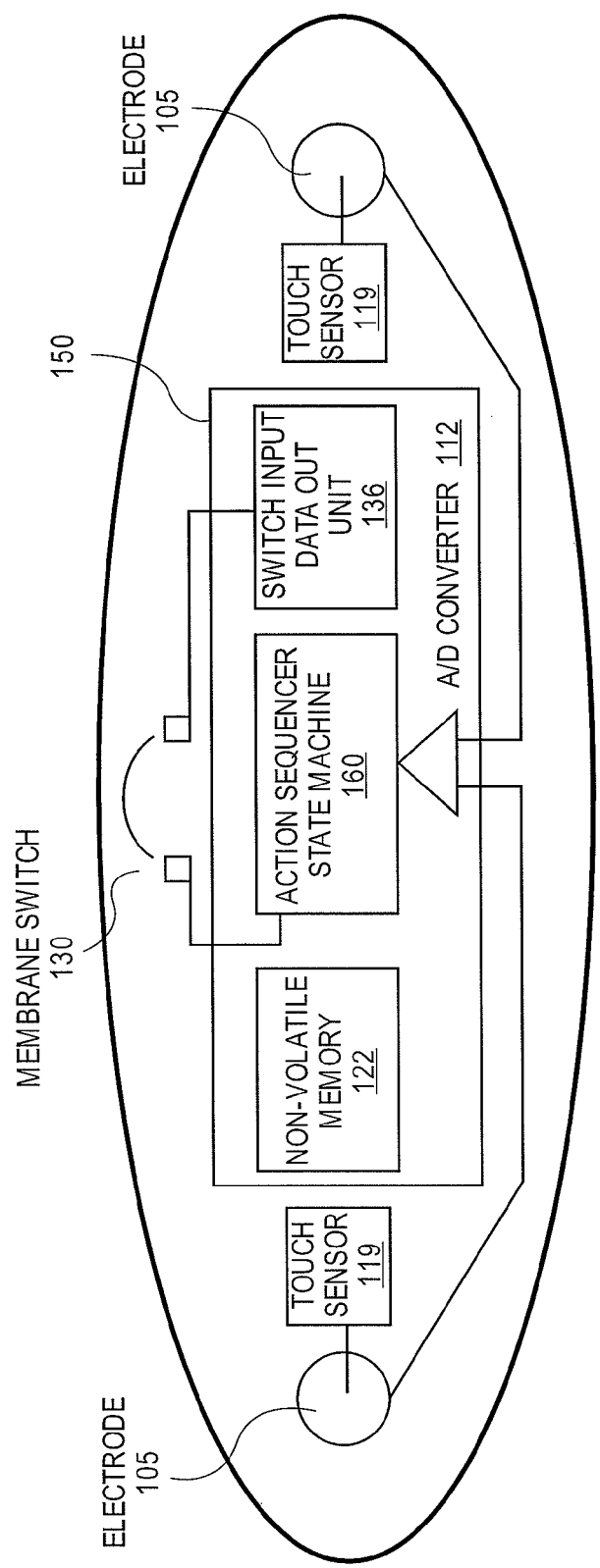
FIG. 4 the basic layout of components in a continuous cardiac monitor.

FIG. 4 illustrates basic physical layout of the components in the cardiac monitor 100. Once properly positioned to detect the ECG signal of a mammal, the ECG signals from the mammal are picked up by the electrodes 105. As described elsewhere, the touch sensors 119 may be used to ensure that the device is properly attached before initiating continuous monitoring. The analog to digital (A/D) converter 112 converts the incoming analog ECG data to digital binary numbers that are a raw numeric representation of the ECG signal. The action sequencer state machine 160 directs the flow of information to either memory 122 or to the switch input/data output unit 136. The membrane switch 130 may be used as an activation or event notation button or switch to increase the fidelity of the signal being continuously recorded.

Another unique feature of the present invention is the selection and use of electronic components that mirror the simple operations being performed by the device. A state machine is a block of custom designed, specific function, sequential control logic, consisting of one flip-flop per binary output state. State machines do not contain central processing units (CPU). One common electronic component that is more powerful than a state machine is a microcontroller. A microcontroller contains a simple CPU that incorporates common peripherals on a chip. A typical microcontroller will incorporate many system level features, such as 110 ports, timers, counters, Pulse Width Modulated outputs, serial ports to support special bus types such as USB, CAN bus, I2C bus, UARTS, watchdog timers, reset circuits, brown out detectors, memory interfaces, low voltage detectors, clock circuitry and analog to digital converters. Not all microcontrollers will incorporate all these features, but any CPU that incorporates one or more of the above peripherals is generally considered a microcontroller. Another common electronic component that is more powerful than both state machines and microcontrollers is a microprocessor. A microprocessor is a programmable digital electronic component that incorporates a more powerful CPU and as well as a variety of complex logic functional elements both within the CPU, and surrounding the CPU to support its programmable functionality. A microprocessor must be programmed to become functional. Additionally, the CPU also contains an arithmetic logic unit (ALU) which performs basic math functions, such as addition, subtraction and multiplication, and an accumulator to store results. External to the CPU are various control and timing circuits, instruction execution units and decoders, memory interface and a variety of registers for temporary storage of data.

The total number of logic gates on various electronic devices is useful as a gauge to the relative capability of a device to perform complex tasks. In general, as the number of logic gates in a device increases, so too increases the ability of that device to perform more complex tasks. In general, up to about 10,000 logic gates are provided in state machines; about 20 k-100 k logic gates is a typical range for microcontroller devices and about 1-1.5M or more logic gates are provided in microprocessor devices. For this reason, intermittent cardiac monitoring systems that operate QRS detection and triggering algorithms and the like while processing real time ECG data require the processing capability of a microprocessor or microcontroller device.

On the other hand, the simple detect-store-offload operations performed by the state machine described herein would likely require only about 1000 logic gates. Since so few logic gates are needed to perform continuously recorded cardiac monitoring, a state machine is the best fit device when viewed in terms of resource utilization to execute the defined functions. As such, it is believed that the action sequencer, when adapted to operate as described, will have a resource utilization ratio of between 95% to 100%. The high resource ratio is due to the fact that the state machine offers a logic device tailored exactly to execute the defined functions. It is believed that if a microcontroller device or microprocessor device were used to perform the action sequencer functions, the resource utilization of those devices would be less than 50% and likely between 5% to 15%. From a resource utilization perspective, microcontroller and microprocessor devices are a poor design choice. Absent additional processing requirements, one of ordinary skill in the field of computer design would not select a microprocessor or microcontroller device for the continuous cardiac monitoring applications of the present invention. The resource utilization of such devices is so low that such devices would be poor design choices and would be contrary to accepted engineering resource utilization guidelines.

Figure 5:
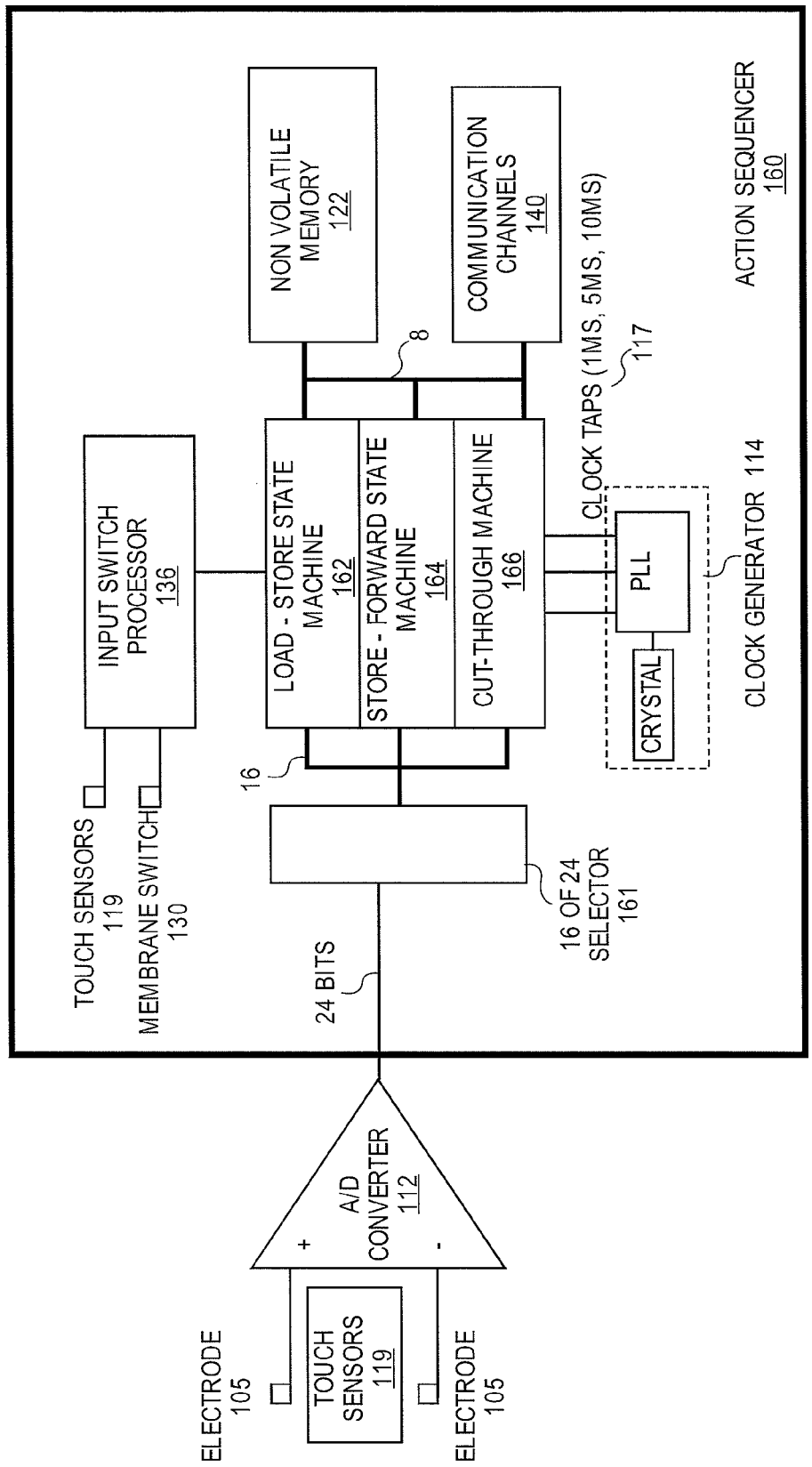
FIG. 5 is a schematic diagram of an action sequencer embodiment.

FIG. 5 is a schematic diagram of an embodiment of an action sequencer circuit 160. The action sequencer circuit 160 controls the operation of the electrical components of the continuous cardiac monitor 100. The sequencer circuit 160 directs the sequence of action, or steps, necessary for signal acquisition and disposition. Electrodes 105 provide continuously detected ECG information to the A/D converter 112. The touch sensors 119 may be used to ensure that the electrodes are attached to a surface before allowing monitoring to proceed. In an embodiment using a 24 bit A/D converter 112, no amplifier circuitry is needed. Typically, 8 bits are used for most bio-signal recording. The range is selected via the 8 to 24 bit selector 161 under the control of the action sequencer. 8 bit resolution is available throughout the 24 bit range in any adjacent 8 data lines. Thus, scaling, or amplification is replaced by selecting the correct range of 8 within the 24 bit span. Additionally, the 24-bit to 8-bit selector serves as a scaler to keep the signal excursions within the numeric range of the A/D converter, or to provide image scaling for the end user.

FIG. 5 schematically represents three simple timing converter state machines 162, 164 and 166 included in the action sequencer 160. The action sequencer design consists of a load-store and forward architecture with a cut-through mode for real time transmission. In one embodiment, the action sequencer activation occurs when the touch sensors 119 applied to the electrodes 105 sense that the continuous cardiac monitor 100 has been applied to mammal skin, and, at the same or about the same time, the membrane button 130 or event notation button 131 is pressed for the first time. In one embodiment, both electrode sense and button activation must occur to activate the action sequencer 160.

The load-store state machine 162 sequences the data from the A/D converter to the memory every chosen clock cycle (i.e., 5 ms). When needed to offload data from memory, a store and forward state machine 164 clocks stored data from the memory, and sends it to the communications channel 140 where it is transmitted at a much higher speed than when recorded. A cut through mode state machine 166 allows the data to be obtained directly from the A/D converter and transmitted, without use of the memory element, providing a means to transmit data in real time. A clock circuit 114 also shown. The clock circuit 114 generates and sets the timing of operations performing within the continuous cardiac monitor 100. The clock generator 114 provides three clock taps 117 to allow different clocking times to be used in the action sequencer. Exemplary clock tap values are 1 ms, 5 ms and 10 ms but other values may be used. The clock circuit 114 also ensures data is written into the memory 122 at the same rate the A/D converter 112 produces them.

The same clock is used to produce similar timing for the disposition side of the data. When a user requires access to the stored data, an inverse process is initiated (e.g., a push button, or other electrical request). Data from the memory is read out, and the data disposition function sends memory data directly to a data port. The data port is any suitable digital or analog form of direct transmission to a conventional reading device using a suitable adapter. Examples of suitable adapters include any high speed communications interface that can be adapted to a small connector inside the device, will be suitable for data transmission. These communication protocols are can be either serial or parallel, but due to the number of wires in a parallel interface and the desire to maintain a small footprint design, a serial communications protocol is preferred. These serial protocols can be simple clocked 2 or 3 wire interfaces, such as I2C (make the 2 a superscript) by Philips, or SPI by Freescale. More complex alternatives include RS-232, RS-422 ore RS-485 serial protocols, or even higher speed, and higher complexity SERDES (serializer-deserializer) type interfaces. These are the most preferred embodiment of the communications channel, as they provided the fastest means of transferring a large amount of data. SERDES based communications include USB 1.1 and USB 2.0, IEEE1394 (known as Firewire) 10, 100.1 Gigabit Ethernet.

Figure 5A:
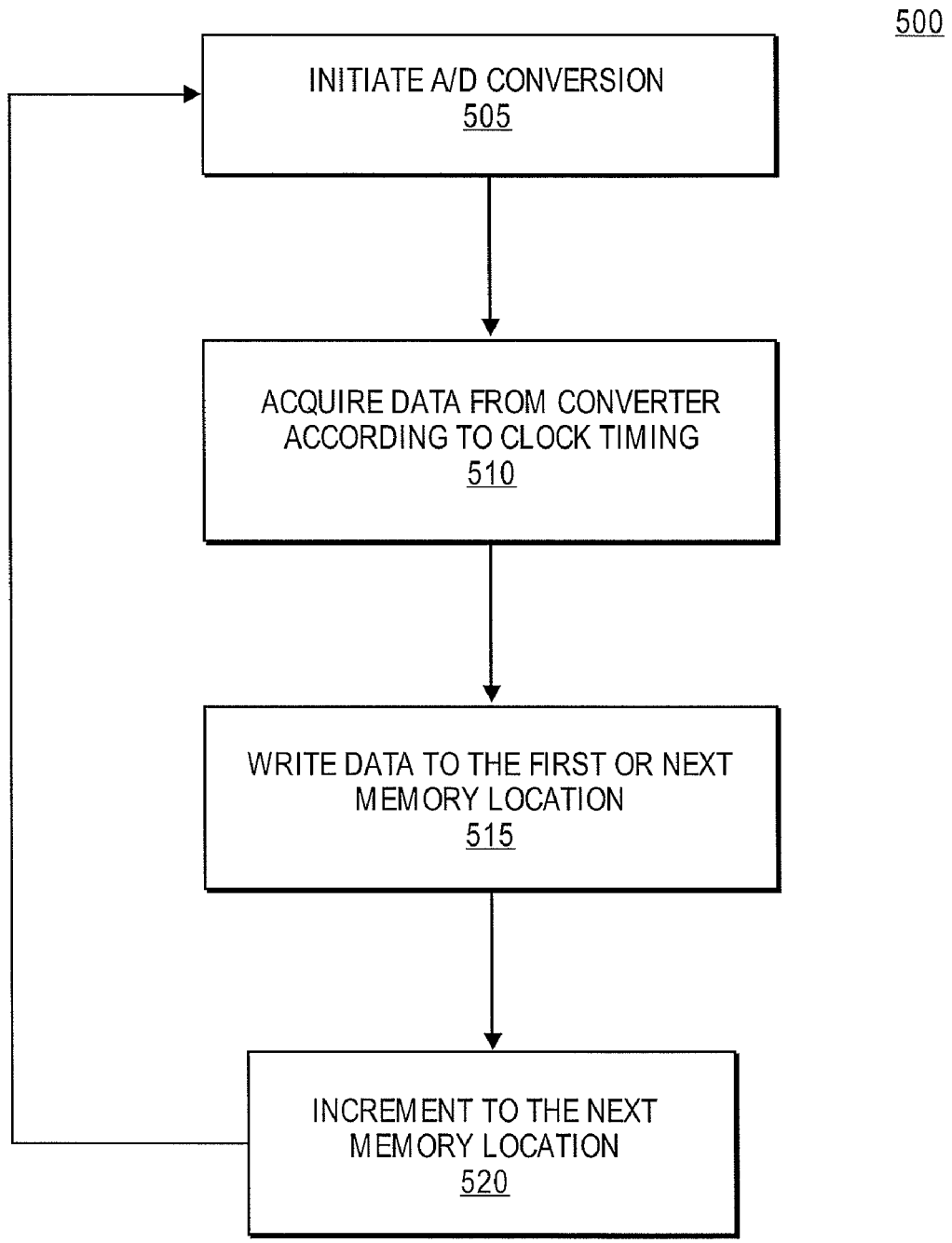
FIGS. 5A and 5B illustrate, respectively, exemplary memory read and retrieval steps.

Turning now to FIG. 5A, flow chart 500 illustrates an exemplary read operation to store signals received from the electrodes. During a read operation, the following steps are done one after another by the action sequencer:

Initiate A/D conversion (step 505)
Acquire data from the A/D according to clock timing (for example, 5 milliseconds) (step 510)
Write the data to first or next memory location (step 515)
Increment to next memory location (step 520)
REPEAT to step 505

This process is initiated when the device is placed on the patient.

The sample rate used in embodiments of the present invention is based on the Nyquist sampling criteria, and the maximum frequency of interest. Typical rates to digitize and sample the data are from approximately 5 ms to 10 ms. When a patient perceives an arrhythmia symptom, a event indicator 131 is activated by squeezing contacts on the device (FIG. 13A), pressing a button (FIG. 13B) or in any other suitable manner to register perception of a symptom. Additionally, the membrane switch 130 may be used as an event indicator. When the event indicator is activated, the sample rate is increased. In one embodiment, the sample rate during a period of high fidelity recording is about half the sample rate during normal continuous recording. In one embodiment, the high fidelity sample rate is from about 2 ms to about 5 ms.

During typical operation, the action sequencer operates at 100 samples per second with 8 bit resolution. During high fidelity recording periods, 16 bits resolution and 200 samples per second may be used. The high fidelity recording mode is activated by the patient pressing, squeezing or otherwise activating an event button 119 or 130 or 131 on the monitor. The button 119 or 130 may be electrically connected to an input line of the action sequencer state machine 160. As a normal function of the action sequencer is to sample the switch input along with the ND converter, the state machine will immediately register and latch the button pressed state, and commence the specific series of the microcoded operating sequences that switches the action sequencer to record in high fidelity. In one embodiment, this process doubles the rate of the acquisition of sampling the data by switching to a faster tap of the internal clock, and commences loading 16-bits, or two bytes, instead of one byte from the 24-bits available, and forwards the data to storage memory 122. One skilled in the art of digital logic design will recognize that this is a straight forward implementation task with proper design of the state machine microcode.

For an exemplary 30 day continuous monitoring period, recording 100 samples per second at 8 bit resolution will require storage capacity of about 259.2 megabytes. If the sample rate doubles to about 5 ms over the entire month, about 520 megabytes of storage are needed. Using 10 bits instead of 8 bits increases required storage amounts by about 25%. As such, an entire month's worth of high fidelity (e.g., 10 bit data/5 ms sample rate) continuous ECG data requires less than a gigabyte of memory.

The amount of memory required in a continuous cardiac monitor may also vary depending upon patient perceptions of cardiac events and event indicator use. A typical event indicator occurrence will increase recording signal fidelity for 5 minutes, for example. Minimally, on a day when no cardiac events are perceived and the device records at a typical recording rate, a standard daily recording with a 10 ms sample rate at 8 bits, would need consumes 8.64 megabytes of memory per day.

If a patient perceives more events during a day, assume 4 button presses per day in this example, where 4 high fidelity periods of 5 minutes each have been recorded and! the high fidelity sample rate is chosen as 5 ms sample rate at 16-bits per sample, then additional memory storage is 200 samples/sec×2 bytes/sample×60 sec/min×20 minutes=additional 480K bytes of storage, or about a total of 9 Megabytes per day.

After the monitoring period is completed, the device is removed from the mammal and the data stored in memory 122 is retrieved. Data stored in memory 122 may be retrieved by any suitable technique. For example, the electronics may be removed from the housing and the communications port 140 accessed via an appropriate connector as described above. Alternatively, the housing 152 may be punctured to create an opening in the vicinity of the port 140. A suitable connector may attach to the port 140 using the opening created in the vicinity of the port 140.

Figure 5B:
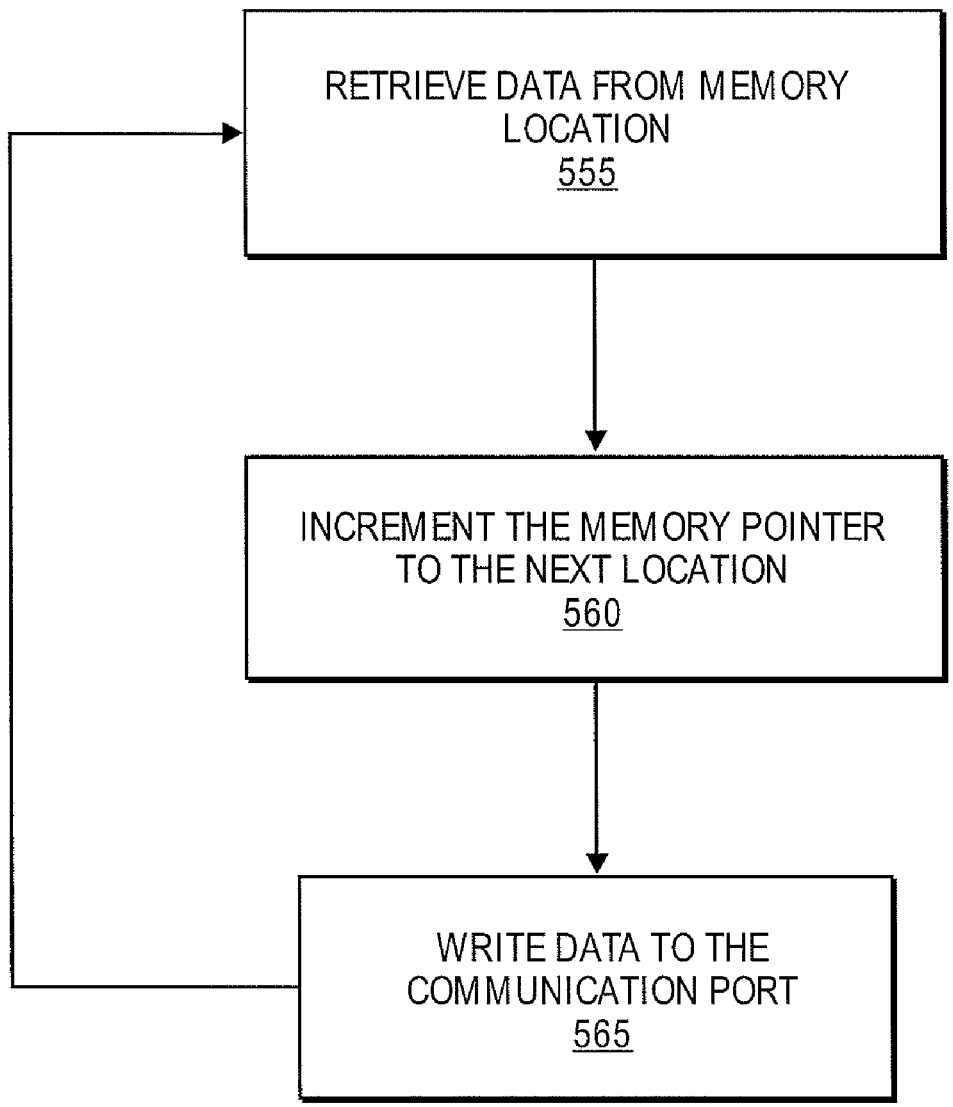

Once the port 140 is accessed, FIG. 5B illustrates the process for an exemplary data disposition or retrieval operation. For the data disposition operation 550, the sequencer 160 does the following steps, moving from step to step each clock cycle:

Retrieve data from memory location (i.e., first or next location) (step 555)
Increment the memory pointer to the next location (step 560)
Write the data to the hardware port (step 565)
REPEAT to step 555

Once initiated, a data disposition operation runs until the last memory location is reached, or the last valid data sample is reached, whichever comes first. While described above as serial operations, the data acquisition and disposition cycles may be run simultaneously if desired. Once the continuous ECG data is removed from the memory 122, the continuous ECG data may be processed using any of a wide variety of available techniques and programs for analyzing ECG data. Many upstream processing algorithms are commonly PC based programs. Monebo Technologies, Inc. of Austin, Tex. is an example of a company in the business of creating and selling heart health assessment signal processing programs. Other companies write their own proprietary algorithms, which are included with proprietary monitoring systems.

Examples of proprietary processing programs include the Medtronic's PaceArt Arrhythmia System, Instromedix Gems and HeartMagic PC based software, Philips Medical Digi-Trak Plus Holter monitoring systems and TraceMasterVue ECG management systems.

Figure 6A:
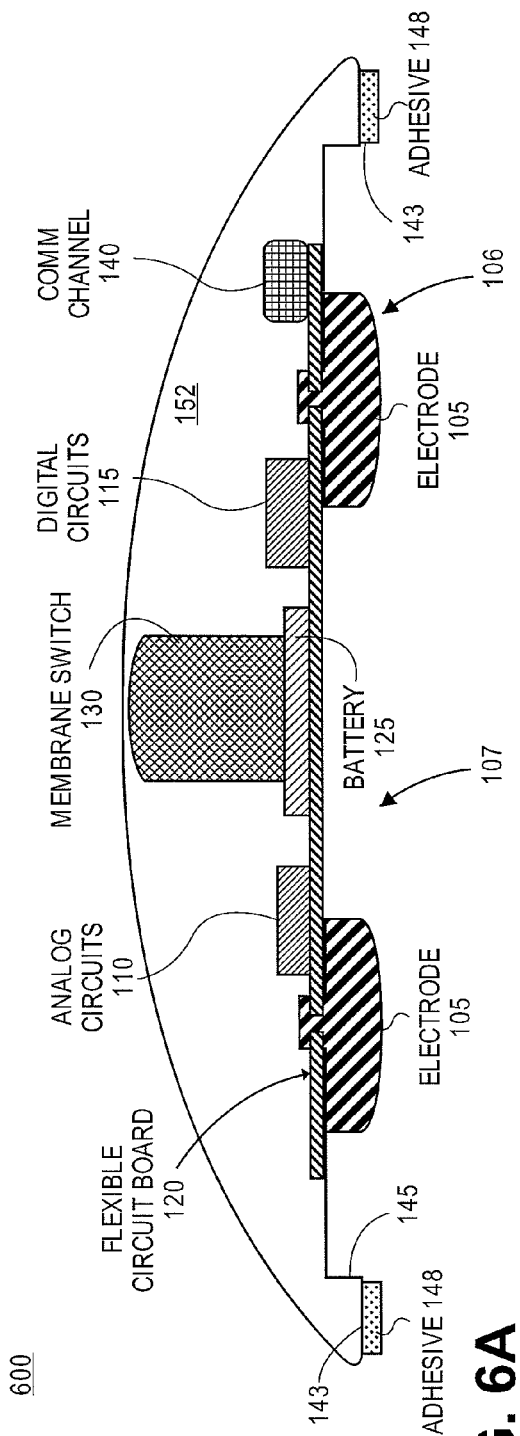
FIGS. 6A-6D illustrate various views of continuous cardiac monitor embodiments having a single electrode pocket.
Figure 6B:
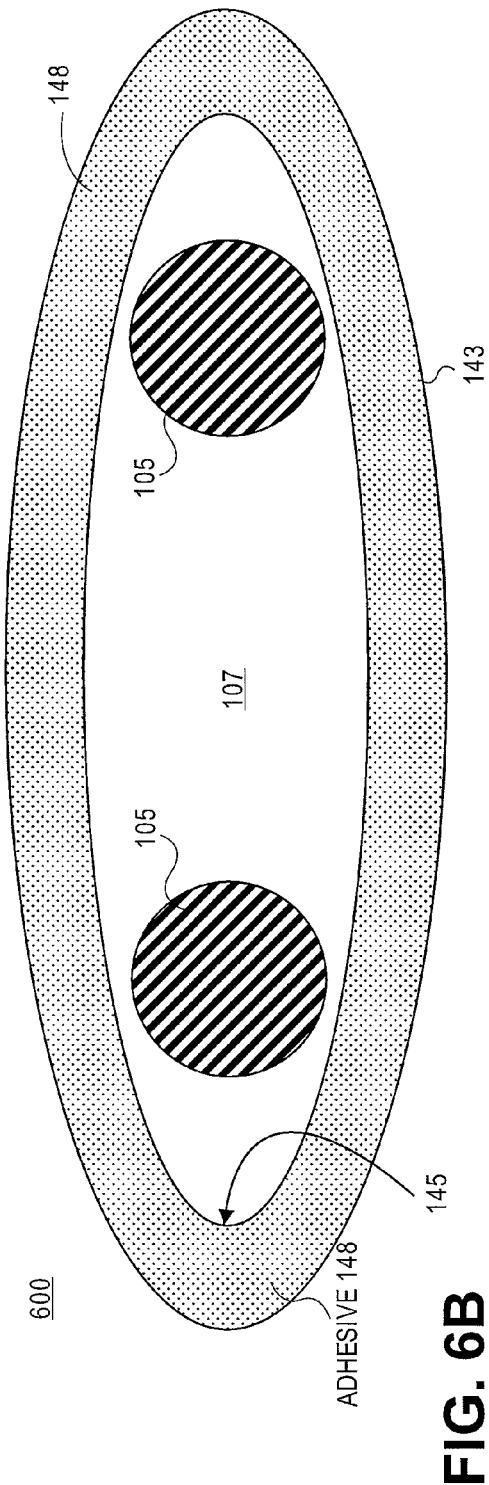
Figures 6C, 6D:
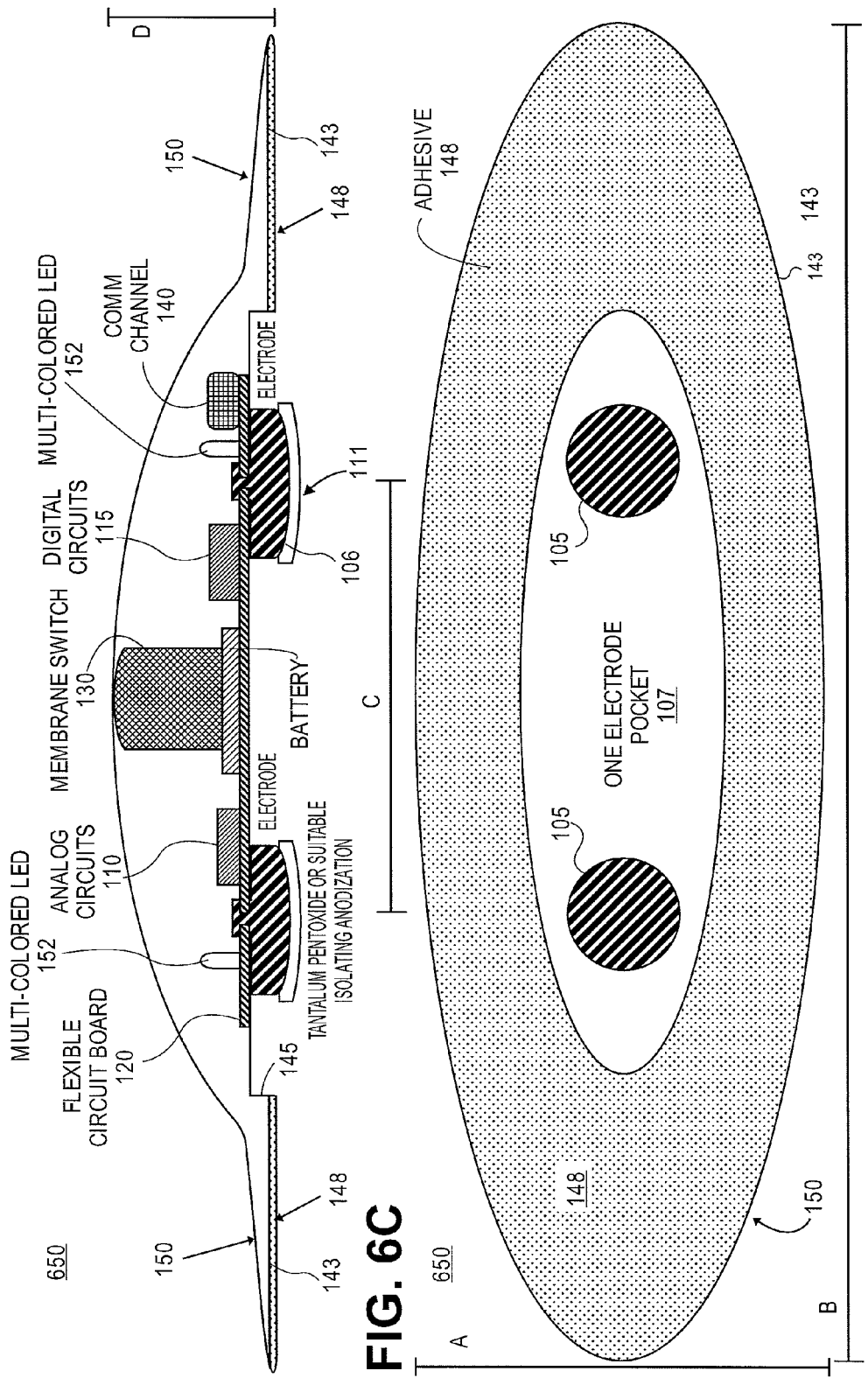

FIGS. 6A-6D illustrate continuous cardiac monitor embodiments having a single dedicated electrode pocket 107 with a sealing rim (best seen in FIGS. 6A and 6B) or a tapered thickness flexible lip (best seen in FIGS. 6C and 6D). FIGS. 7A-7D below illustrate similar sealing and affixing surfaces around the use of dedicated electrode pockets 117.

FIGS. 6A and 6B illustrate side and bottom views respectively of a continuous cardiac monitor 600. The continuous cardiac monitor 600 includes the electronic components and performs the functions described above with regard to FIGS. 3-5B. The continuous cardiac monitor 600 includes a sealing surface 143 and a rim 145, such that when the monitor 600 is affixed to a mammal, a single dedicated electrode pocket 107 is formed. The single electrode pocket 107 is used to form the watertight chamber that will contain the electrodes during the monitoring period. Two electrodes 105 are shown, but more electrodes could be provided depending upon the specific monitoring to be performed. As best seen in FIG. 6B, the adhesive 148 is coextensive with the surface 143. In use, when the adhesive 148 is affixed to the mammal, the rim 145 extending from the surface of the housing forms a watertight chamber, here the electrode pocket 107, around and including the two electrodes 105. FIG. 6A also illustrates that in use a single watertight enclosure 107 would be bounded by the interior of the chamber 107 and the skin of the mammal.

FIGS. 6C and 6D illustrate side and bottom views respectively of a continuous cardiac monitor 650. The continuous cardiac monitor 650 is similar in construction to the monitor 600 with the addition of the flexible seal 150 that extends beyond the central portion of the housing 133 into a tapered perimeter. The flexible seal 150 increases the amount of surface area available for affixing and sealing the monitor to the mammal during the monitoring period. Monitor 650 includes a sealing surface 143 that when the monitor 650 is affixed to a mammal, a dedicated electrode pocket 107 is formed, as described above in FIG. 6A. As best seen in FIG. 6D, the adhesive 148 is coextensive with the surface 143. In use, when the adhesive 148 is affixed to the mammal, the surface 143 forms a watertight seal that forms the dedicated electrode pocket 107, around the two electrodes 105. FIG. 6D also illustrates that in use watertight enclosures 107 are provided around both electrodes 105.

FIG. 6C also illustrates an alternative electrode embodiment. One challenge in long term monitoring is that mammal skin cannot easily tolerate long term application of conventional electrodes, typically comprising chemicals such as sliver chloride embedded in an active, conductive electrolyte. These types of conventional electrodes also deteriorate in performance over time as the electrolyte dries out or becomes contaminated. Although it is contemplated that more hypo allergenic electrodes and companion electrolytes may be developed, and could be used effectively in the current device, one embodiment of the present invention uses dry skin, capacitive or non-reactive ohmic contact electrodes. In one embodiment, electrodes 105 may be adapted for long term applications by constructing the electrodes from stainless steel, or Tantalum. Additionally, a uniformly thin film coating comprising Tantalum Pentoxide ($Ta_2O_5$), which is an inert thin film of glass may be used. This thin coating 111 is illustrated in FIG. 6C on the rounded surface 106 of electrodes 105. The drawing is not to scale and the thickness of the coating is exaggerated for purposes of illustrating its location.

The thin coating may be applied by conventional coating means. Alternatively, the so called super coating process developed by the Sanford Process Corporation may be used. The super coating process provides a hard coating of penetrating anodization of aluminum. With either process, DC resistances of more than 1 G ohm is achieved, and the capacitor formed ranges from 0.01 microfarad to 0.1 microfarad. Although ranges can vary, the capacitance of the electrodes in a monitor should be matched in value for best common mode rejection.

There is another physical differentiating characteristic in the electrode designs used in the present invention. Since the electrodes only minimally protrude beyond the surface of the housing they are also unlikely to cause skin breakdown since they are not exerting significant enough pressure on the skin. Further, as there are no significant sharp edges on these electrodes and as the contact area with the skin is spread over the electrode surface, skin breakdown is unlikely since there are no focal or sharp pressure points. There are no sharp square edges as found in common intermittent monitors. Sharp edges may be tolerated for short monitoring periods but are not suited to long term continuous monitoring applications. In contrast, electrodes 105 include a softer rounded edge 106 that helps to mitigate or minimize irritation during long term skin contact. As best seen in FIG. 6C, the surface seen in profile has a gentle curve 106, typically with a smooth radius that is free from sharp edges. The dome shape spans the top of the electrode 105 in the region of skin contact to provide good signal contact without edge irritation while reducing triboelectric noise generated by motion of skin in contact with sharp corners (as is common in conventional monitors).

FIG. 6C also illustrates an LED indicator 610 useful to show proper operation of the monitor as the monitoring period progresses. In this embodiment, low power, multicolored light emitting diodes 610 are provided as state machine status indicators. When the device is first manufactured and in storage, the LED is inactive. Once applied and the membrane switch 130 is pressed for the first time, the LED indicator activates when the ECG of the mammal wearing the device is detected. The LED indicator may produce a green burst flash (or other suitable color, such as blue) once every 5 seconds, or at some other interval. In one embodiment, a longer flash interval period is used to preserve battery energy. Intervals may be up to about 1 minute apart. The LED may also be configured to provide a continuous indication as long as the ECG of the mammal is detected. A continuous indication in this context refers to an indication that is persistent during the monitoring period. As such, a flashing indicator could be considered a continuous indication if the flashing remained during monitoring. A continuously illuminated LED and the like would also be suitable continuous indications.

If one or both of the electrode touch sensors detect a higher than 1 Mohm impedance level, the flashing LED changes to yellow (or other suitable standard color), indicating a bad skin contact, and a poor quality recording would result, so the patch needs to be changed. This may occur on initial application, or anytime during the time the device is worn.

Once the memory is full and the device can longer record, The flashing LED changes to red (or other suitable designated color), indicating to the patient that the patch must be sent or carried back to a location designated by the physician, so that the recorded data may be retrieved. Other colors may be beneficially used for other key indicators, such as "one day left to record". Once removed, the LED stops flashing to conserve power.

FIG. 6D also illustrates various dimensions useful in describing continuous cardiac monitors. While described in terms of the embodiment of FIG. 6D, the design parameters and general dimensions that follow are applicable generally to continuous cardiac monitor embodiments. Several general device dimensions are illustrated in FIG. 6D. Device dimensions vary in sizes, depending on the size of the mammal. Width dimension A may effectively vary from 2 cm to 6 cm with 4 cm+/−2 being a suitable range. Similarly, the overall length dimension B may vary from 5 cm to 10 cm, with 7 cm nominal. The dimension C indicates electrode spacing. The spacing and placement of the electrodes is critical for two reasons. First, the minimum separation is necessary to pick up an ECG differential signal without outside amplification. This separation varies by mammal, but always must meet a minimum separation of 5 cm for the smaller mammals, to 6 cm for humans, and larger mammals. Second, the electrodes must be well inside and away from the edges of the adhesive patch, to maintain top performance and prevent outside contamination. Embodiments of the present invention provide rims, lips, tapered surfaces alone or in various combinations to ensure the desired electrode operating environment is maintained during the monitoring period. In one embodiment, the dimension C varies linearly and proportionally with the overall length of the patch. In one embodiment, the ratio of B to C would be about 1.25. Additionally, designs may be altered to provide an additional design parameter that the electrode must be at least 8 mm from any edge of the monitor. This design parameter ensures that at least an 8 mm sealing edge is provided by each electrode. Embodiments of the rims and sealing lips described herein may be adapted to meet this design feature. Additional dimensional information is described below with regard to FIGS. 8A-8C. Moreover, the height, or thickness of the patch is important so that the upper surface of the monitor when affixed to the skin minimizes obstruction of clothing, harnesses or activities. In one embodiment, the range of D dimension values range from 0.5 cm to 1.5 cm.

Figure 7C:
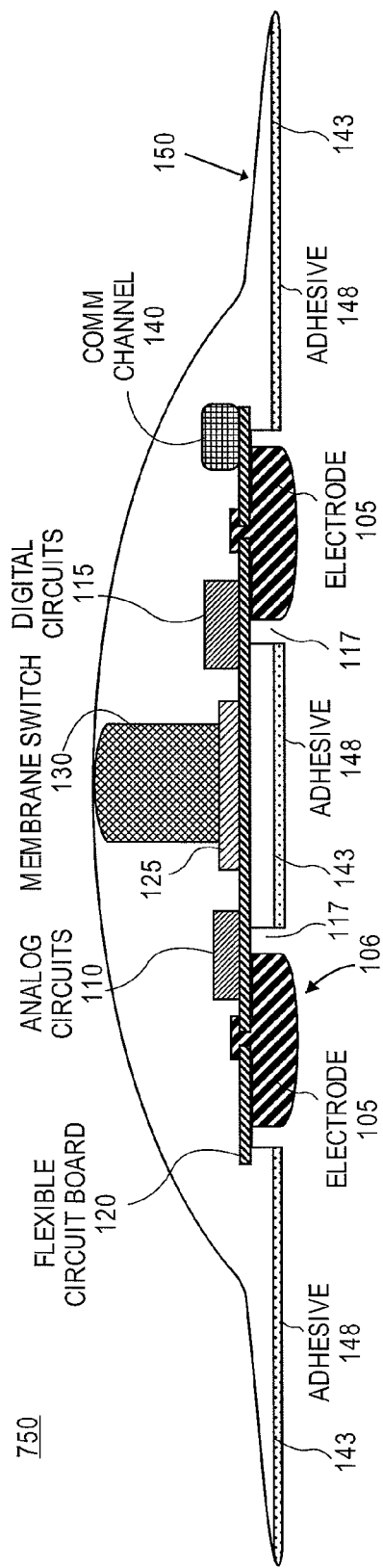

FIGS. 7A-7D illustrate continuous cardiac monitor embodiments having dedicated electrode pockets 117. The continuous cardiac monitors described in FIGS. 7A-7D include the electronic components and perform the functions described above with regard to FIGS. 3-5B. FIGS. 7A and 7B illustrate side and bottom views respectively of a continuous cardiac monitor 700. The continuous cardiac monitor 700 includes a sealing surface 143 and a rim 745, such that when the monitor 700 is affixed to a mammal, dedicated electrode pockets 117 are formed. As best seen in FIG. 7B, the adhesive 148 is coextensive with the surface 143. In use, when the adhesive 148 is affixed to the mammal, the rim 745 forms a watertight chamber; here the dedicated electrode pockets 117, around the two electrodes 105. FIG. 7A also illustrates that in use separate watertight enclosures 117 are provided around each electrode 105.

Figure 7D:
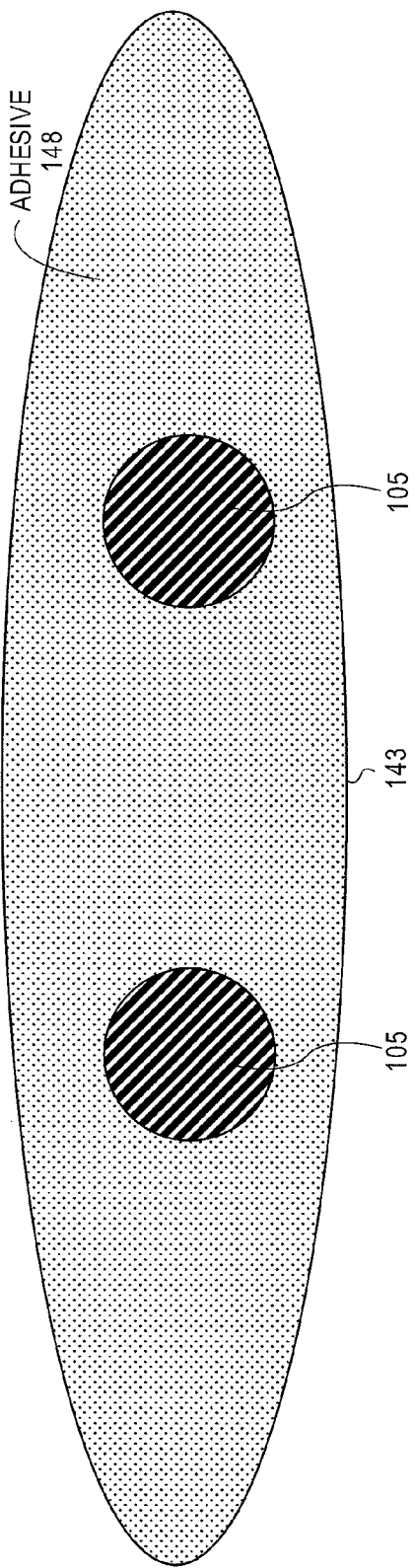

FIGS. 7C and 7D illustrate side and bottom views respectively of a continuous cardiac monitor 750. The continuous cardiac monitor 750 is similar in construction to the monitor 700 with the addition of the flexible seal ISO that extends beyond the central portion of the housing 133 into a tapered perimeter. The flexible seal ISO increases the amount of surface area available for affixing and sealing the monitor to the mammal during the monitoring period, similar to FIG. 6C. Monitor 750 includes a sealing surface 143 that when the monitor 750 is affixed to a mammal, dedicated electrode pockets 117 are formed. As best seen in FIG. 7D, the adhesive 148 is coextensive with the surface 143. In use, when the adhesive 148 is affixed to the mammal, the surface 143 forms a watertight seal that forms the dedicated electrode pockets 117, around the two electrodes 105. FIG. 7D also illustrates that in use separate watertight enclosures 117 are provided around each electrode 105.

Figure 8A:
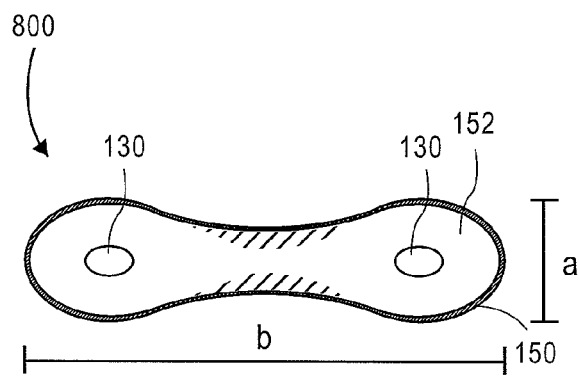
FIGS. 8A-8C illustrate various views of another continuous cardiac monitor embodiment.
Figure 8B:
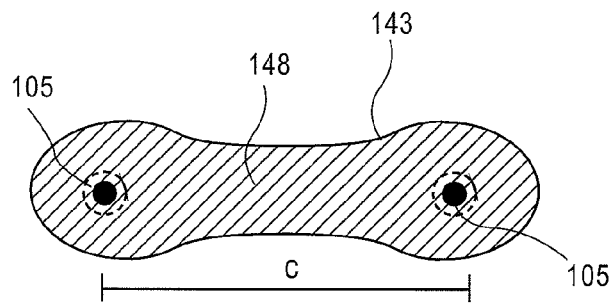
Figure 8C:
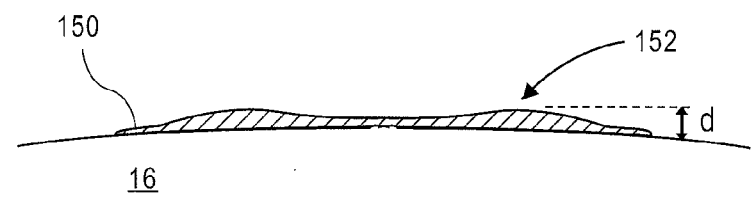

FIGS. 8A, 8B and 8C are, respectively, top, bottom and side views of a continuous cardiac monitor 800 according to an alternative embodiment of the present invention. The continuous cardiac monitor described in FIGS. 8A-8C includes the electronic components and performs the functions described above with regard to FIGS. 3-5B. The cardiac monitor 800 includes two activation or event notation buttons or switches 130 within an elongated housing 152. The dog bone shaped housing extends the length (indicated as b in FIG. 8A) to provide greater variability of electrode spacing (indicated as c in FIG. 8B) while still providing an adequately sized surface 143 to ensure a good seal and long term adhesion. The elongate axis b may provide alternative configurations adapted for monitoring small animals such as dogs and large mammals such as horses where the curvature of the rib cage or other attachment point is subject to wide anatomical variation. Moreover, such designs may be suited to monitoring humans but with the monitor 800 configured to wrap partially around the torso rather than being placed directly over the heart. The indicated a dimension in FIG. 8A may be about 1 inch. The indicated b dimension in FIG. 8A may be about 2-3 inches. The indicated c dimension in FIG. 8B may be from about 1.5 to 2.5 inches. The indicated d dimension in FIG. 8C may be about or less than 0.5 inches.

Figure 9:
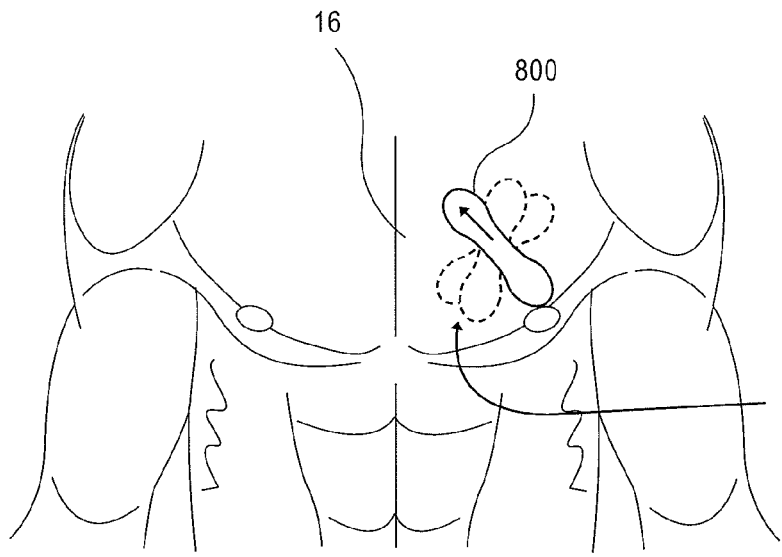
FIG. 9 illustrates the monitor of FIGS. 8A-C in place on a patient.

FIG. 9 illustrates device 800 movement (in phantom) during attachment of the monitor to the chest 16. Once a good signal is received (indicated using the indicators described herein for example) the monitor is affixed to the mammal.

Figure 10:
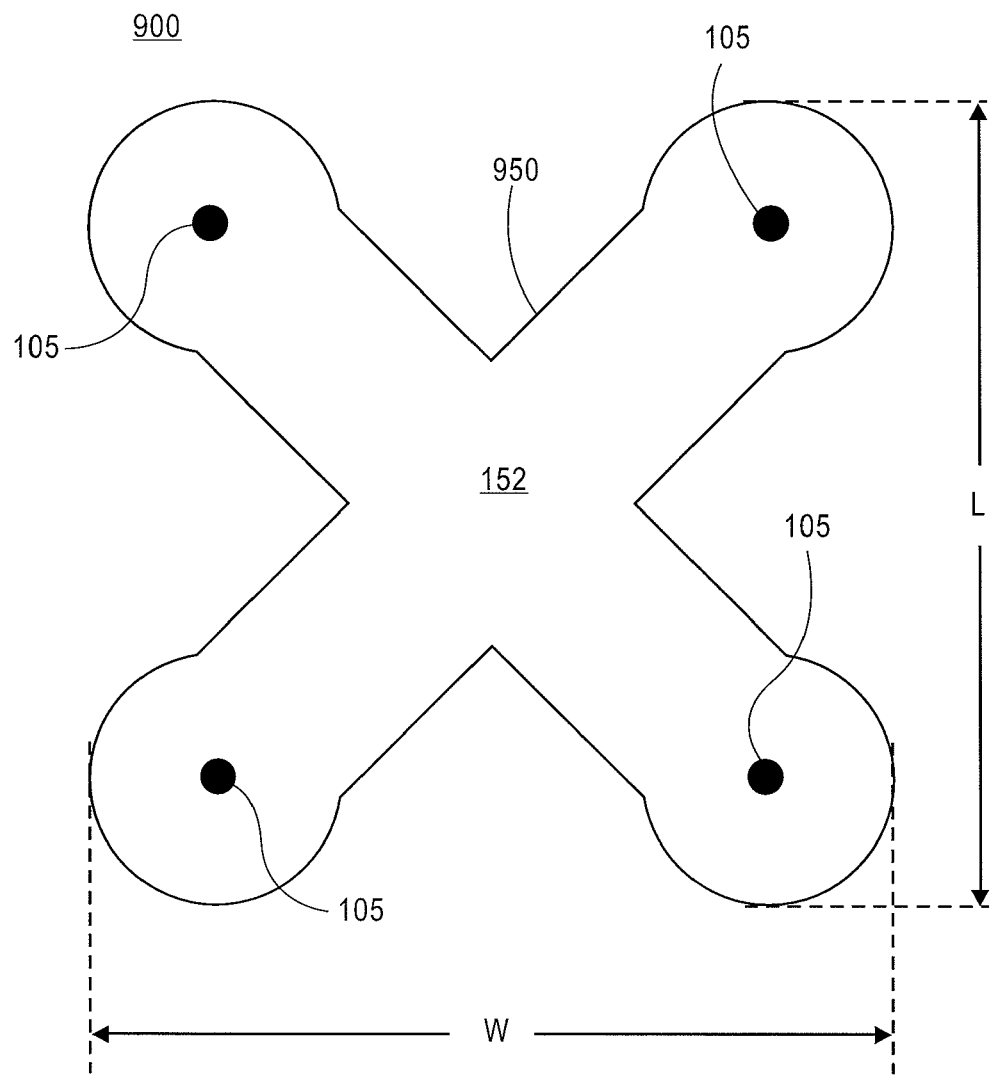
FIG. 10 illustrates another continuous cardiac monitor embodiment.

FIG. 10 illustrates a continuous cardiac monitor 900 according to an alternative embodiment of the present invention. The continuous cardiac monitor illustrated in FIG. 10 includes the electronic components and performs the functions described above with regard to FIGS. 3-5B. The housing 152 in this embodiment includes a plurality of arms 910. Each arm includes a surface 143, an adhesive 148 and an electrode pocket. The electrode pocket may be of any of the types described herein such as single pocket 107 or individual electrode pockets 109. More or fewer arms, the length of the arms and the dimensions L and W may be adjusted depending upon a number of factors, such as, for example, the position of the monitor 900 on the mammal and the size of the mammal. Larger dimensions L and W may be used to adapt the monitor for use on horses or, alternatively, if the monitor is affixed to the back rather than the chest of a human.

Figure 11:
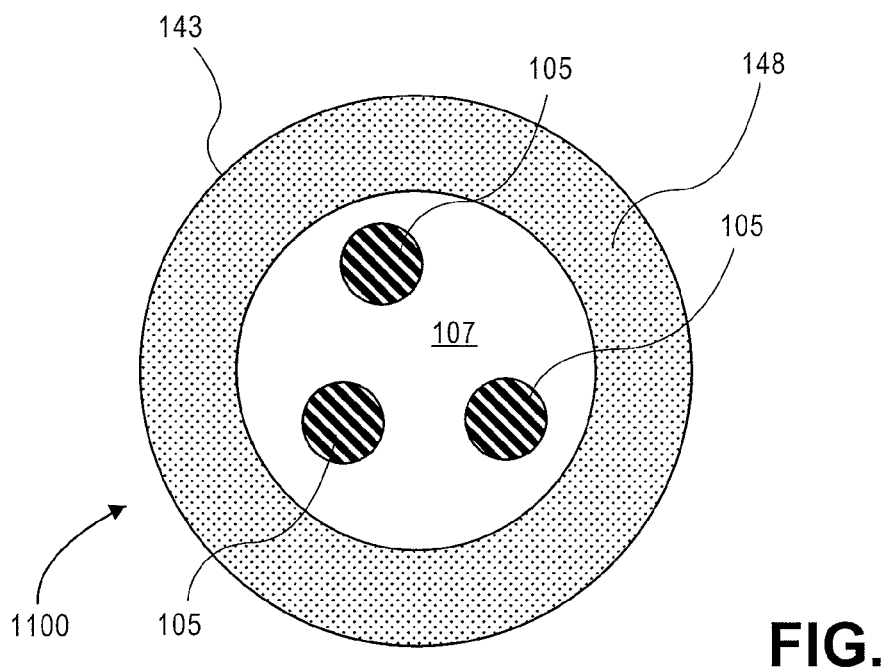
FIG. 11 illustrates another continuous cardiac monitor embodiment.

FIG. 11 illustrates a circular continuous cardiac monitor 1100 according to an alternative embodiment of the present invention. The continuous cardiac monitor illustrated in FIG. 11 includes the electronic components and performs the functions described above with regard to FIGS. 3-5B. The housing 152 in this embodiment is generally circular and includes an annular shaped surface 143 having adhesive 148 thereon. The single electrode pocket 107 in this embodiment includes 3 electrodes 105. Alternatively, the single electrode pocket 107 may be modified into the dedicated form of electrode pocket 117 described above. The dimensions of this embodiment—having more or fewer electrodes—may be well suited to continuous cardiac monitoring applications for large mammals such as horses.

Figure 12A:
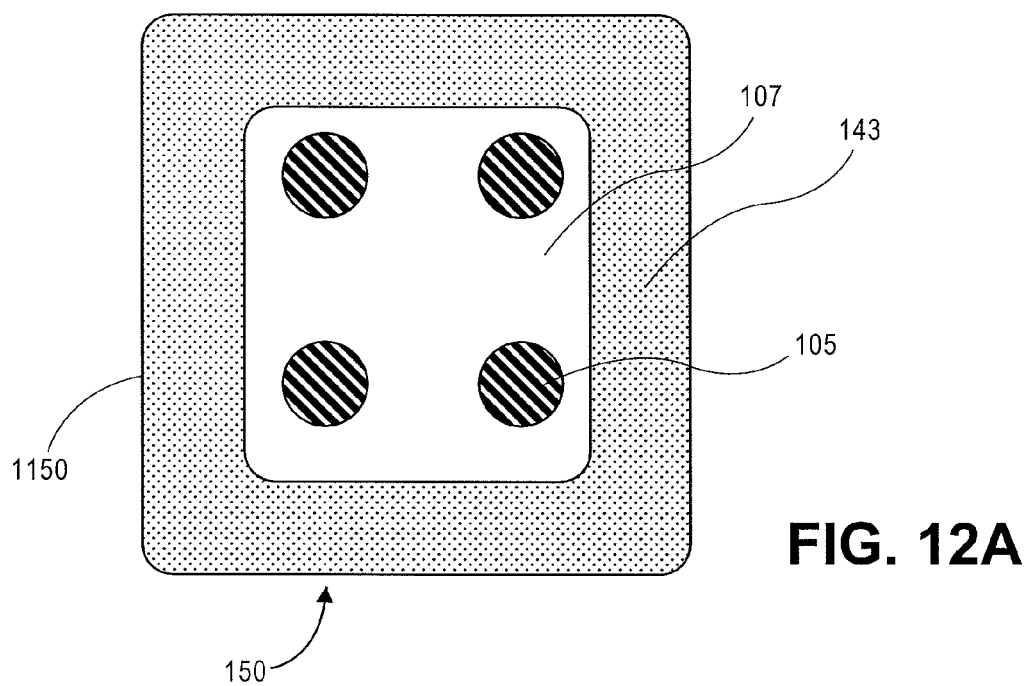
FIG. 12A illustrates another continuous cardiac monitor embodiment and FIG. 12B illustrates the monitor in FIG. 12A in place on the chest.
Figure 12B:
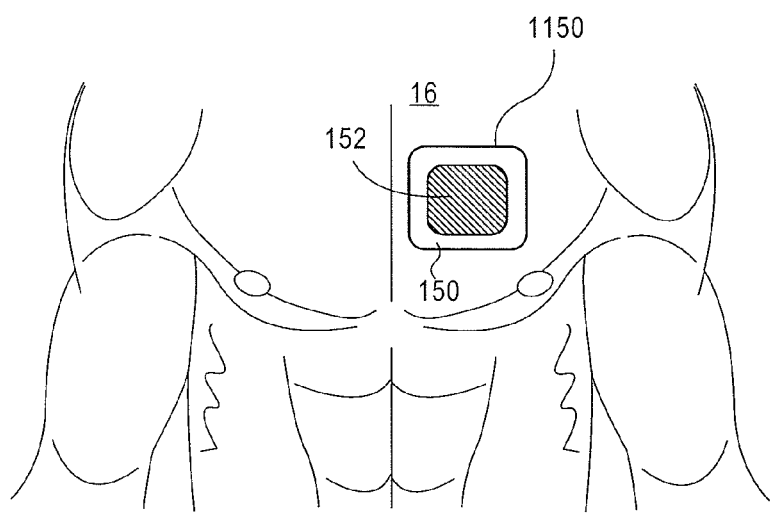

FIG. 12A illustrates a continuous cardiac monitor 1150 according to an alternative embodiment of the present invention. The continuous cardiac monitor illustrated in FIG. 12A includes the electronic components and performs the functions described above with regard to FIGS. 3-5B. The housing 152 in this embodiment is generally rectangular and includes a rim 150 with an adhesive 148 as described above. The single electrode pocket 107 in this embodiment includes 4 electrodes 105. Alternatively, the single electrode pocket 107 may be modified into the dedicated form of electrode pocket 117 described above. The dimensions of this embodiment—having more or fewer electrodes—may be well suited to continuous cardiac monitoring applications for large mammals such as horses. FIG. 12B illustrates an embodiment of the cardiac monitor 1150 in position on the chest 16 to detect cardiac signals.

Figure 13A:
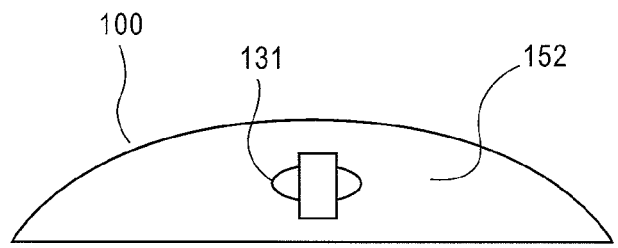
FIGS. 13A and 13B illustrate various event notation embodiments.
Figure 13B:
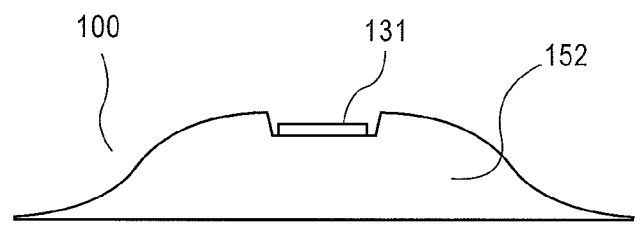

FIGS. 13A and 13B illustrate alternative activation or event notation button or switch embodiments. The continuous cardiac monitors illustrated in FIGS. 13A and 13B include the electronic components and performs the functions described above with regard to FIGS. 3-5B. The membrane switch 130 is one form of an activation or event notation button or switch. An activation or event notation button or switch is any device used by the mammal wearing the: device to indicate the perception of symptoms. An activation or event notation button or switch may be formed in the housing 152 in a manner such that the event notation capability remains accessible for activation while the adhesive is affixed to the mammal. Activation or event notation buttons or switches 130 and 131 are accessible when the device is affixed to the mammal. Activation or event notation button or switch 131 illustrated in FIG. 13A is activated by squeezing the tabs on the button together. This design requires additional action by the user to register the event and may be useful to minimize false event registration. Similarly, the membrane switch 130 described above is below the surface of the housing and requires depressing of the surrounding housing to register an event. The activation or event notation button or switch 131 illustrated in FIG. 13B is similar to the membrane switch 130 except that it positioned below the surface of the housing. As described above, actuation of an activation or event notation button or switch increases the fidelity of the cardiac information stored in the electronic memory. Activation or event notation button or switch activation is stored in the electronic memory with contemporaneous cardiac information. In this way, the cardiac data contemporaneous to the patient's perceived symptoms can be analyzed using the methods described below.

Figure 14:
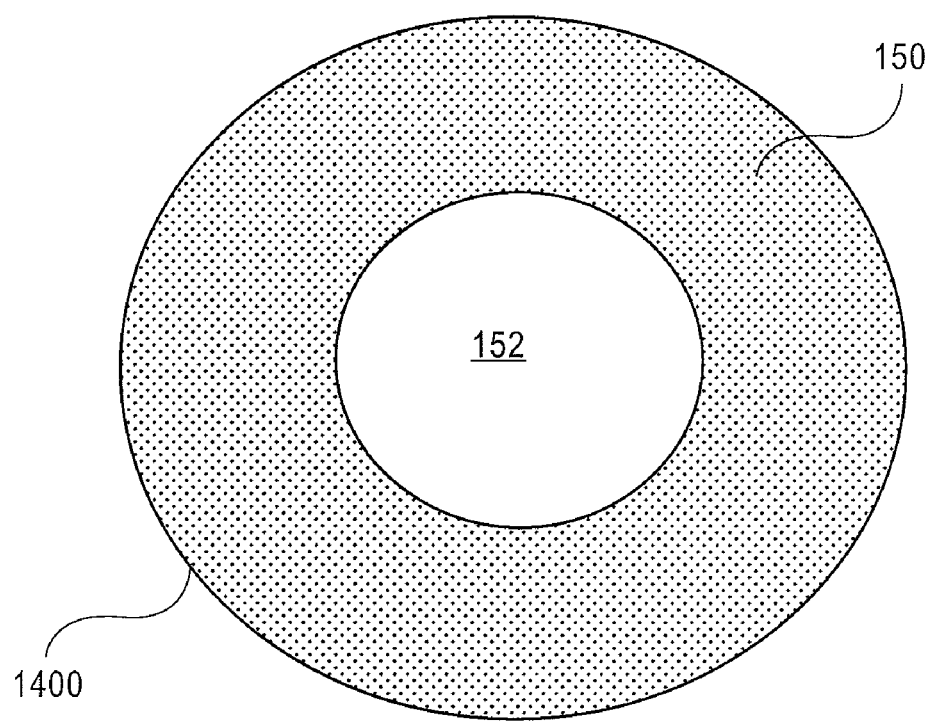
FIG. 14 illustrates another continuous cardiac monitor embodiment.

FIG. 14 illustrates a cardiac monitor 1400 having a circular central portion housing 152. As with previous embodiments, the electronic components are contained inside the housing and the illustrated continuous cardiac monitor in FIG. 14 includes the electronic: components and performs the functions described above with regard to FIGS. 3-5B. In this embodiment, the flexible sealing lip 150 includes pores to enhance long term patient comfort. Similar to how a porous bandage allows air to aid in healing, it is believed that adding pores to flexible lip will enhance breath ability of the skin and lead to greater patient comfort during long term continuous monitoring. Moreover, this or other embodiments of the flexible lip 150, housing 152 or other components have be altered to include pleasing features such as cartoon characters, symbols from athletic teams, mottos, slogans or decorative designs to enhance the visual appeal of the device. Additionally or alternatively, all or a portion of the device may be colored or tinted to either increase the visibility of the device on the mammal (i.e., add a brightly colored pigment to the housing) or decrease the visibility of the device on the mammal (i.e., modify the outward appearance of the device to closely match the appearance of the mammal where the device is to be mounted). Modifications to the outward appearance of the device to closely match the appearance of the mammal where the device is to be mounted include such things as adding pigment to match the mammal skin tone or adding fur or hair to match the fur or hair on a horse, dog or other animal under going continuous monitoring. While described in the context of the embodiment of FIG. 14, these features are not so limited and may be applied to other embodiments of the invention.

Embodiments of the continuous cardiac monitor described herein provide a robust set of patient cardiac data for processing and evaluation. The availability of this data now enables physicians and health care providers with additional methods to evaluate the condition of a patient. Additionally, this new type of cardiac data leads to new processes of maintaining and controlling the flow and availability of the data. These methods will be described with reference to the flow charts in FIGS. 15-19.

Figure 15:
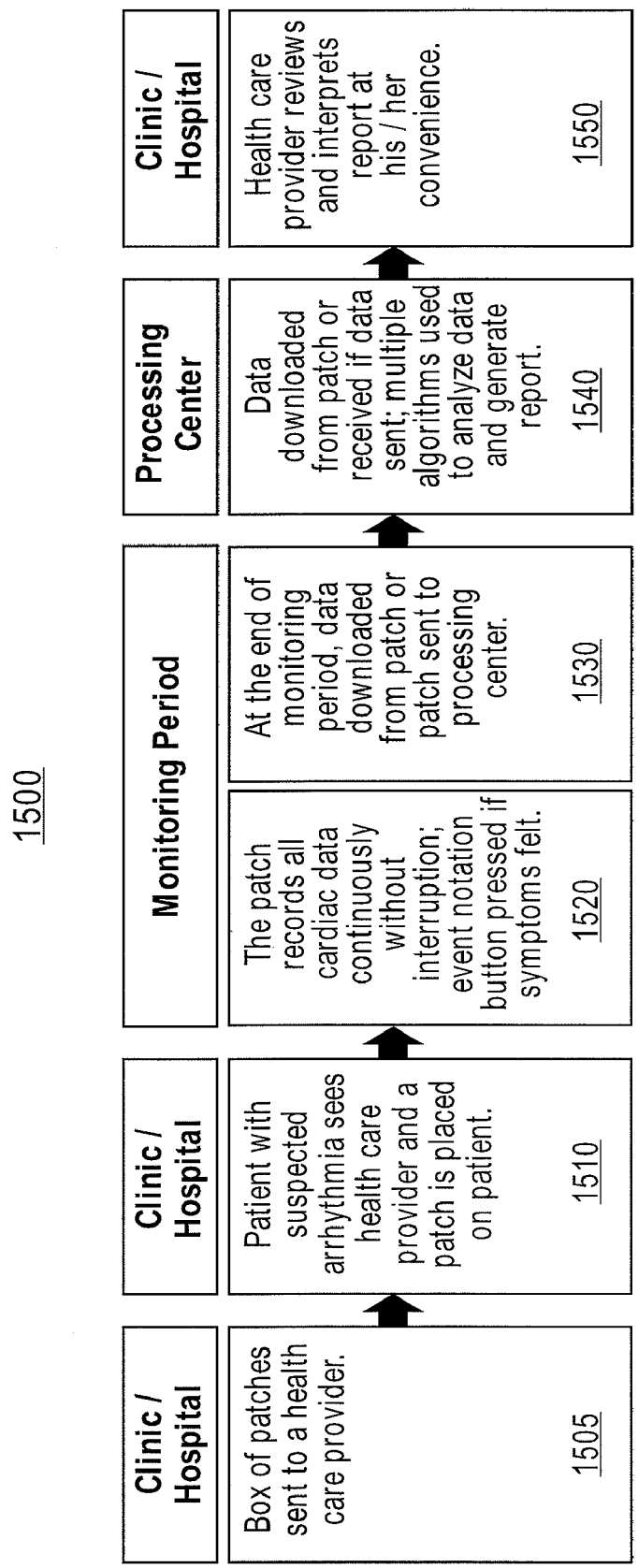
FIG. 15 illustrates a method of obtaining and evaluating continuous cardiac data.

FIG. 15 illustrates a method of obtaining and evaluating continuous cardiac data. First, at step 1505 a box of patches or continuous cardiac monitors is provided to a health care provider at a hospital, clinic or other treatment center. Next, at step 1510, a patient with suspected arrhythmia sees the health care provider. A continuous cardiac monitoring patch is placed on the patient. The physician or assistant logs the application of the patch to the patient, noting the unique patch identification as well as the date and time of initiation of monitoring. Logging initiation of monitoring may be accomplished using a software tracking system in the physician's office, by accessing a database via the Internet or by any other means to document initiation of monitoring. Additionally or alternatively, the patient may also follow a pre-set initiation ritual which includes placing a known marker into the data stream at a specific time after the initiation of monitoring. For example, at 5 pm on the first day of monitoring, the patent may activate the event registration button to provide a way to synchronize the continuous data recording more precisely to the start of data acquisition.

Next, during the monitoring period, the patch records all cardiac: rhythm continuously without interruption (step 1520). Additionally, the patient may note onset of symptoms by pressing the event registration button or switch. Next, at step 1530, at the conclusion of the monitoring period, data is downloaded from the patch at the physician's office, a clinic or other site configured to receive and download stored continuous cardiac data. Optionally, the patient may provide the patch to a processing center, or download and transfer the stored data himself or herself.

Next, at step 1540, continuous cardiac data is downloaded from the patch or received if the data is sent. Recorded patch data is linked to stored patient information. Multiple different algorithms, processing techniques and methodologies may be used to analyze the continuous cardiac data. Based on this analysis, a report is generated. Next, at the hospital or clinic, the physician or health care provider reviews and interprets the report at his or her convenience (step 1550). Importantly, because all of data from the entire reporting period is available, the physician may also access the continuous data to aid in the treatment of a patient. One advantage of having continuous cardiac data—rather than filtered data as in intermittent cardiac rhythm monitors—is that the data may be used to assure a patient that he or she does not have any arrhythmia. A physician reviewing intermittent cardiac rhythm data would need to provide a caveat that the monitor did not detect any arrhythmia. In contrast, a physician who evaluates continuous cardiac data may base his opinion on a review of all cardiac data. The important difference is that with continuous cardiac data the physician—not an algorithm—determines whether a heart beat is abnormal.

Figure 16:
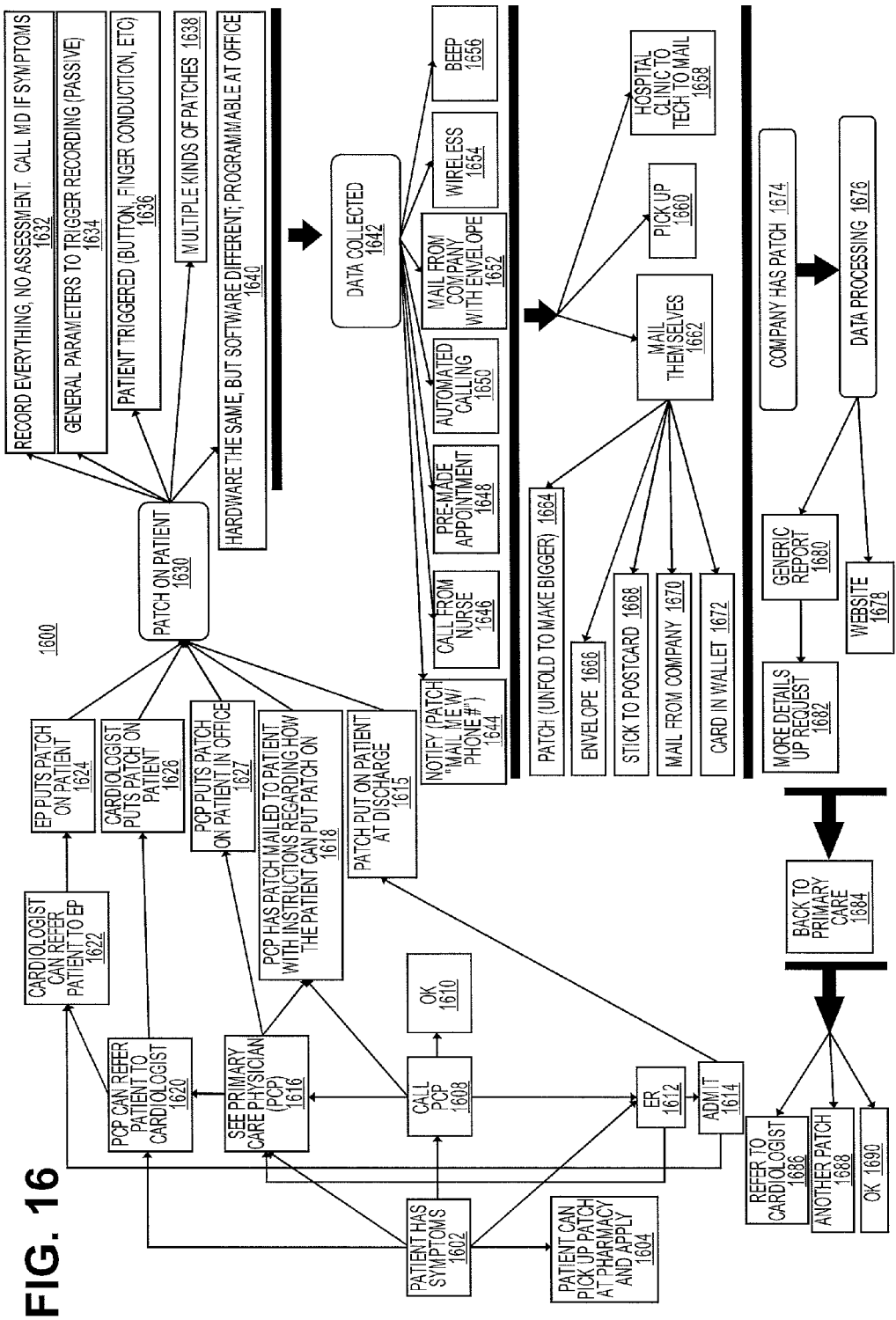
FIG. 16 illustrates a comprehensive method of treatment options available based on the use of continuous cardiac monitors.

FIG. 16 illustrates a comprehensive method 1600 of how the availability of continuous cardiac monitoring devices will enable new methods of treating patients and evaluation cardiac data. Once a patient perceives symptoms of abnormal cardiac activity (step 1602), there are several ways a continuous cardiac monitoring patch may be placed on a patient (step 1630).

The patient may obtain one at a pharmacy and apply (step 1604). A patch may be available from any of a wide variety of locations and under various arrangements. Obtaining a patch from a pharmacy is merely for purposes of illustration.

The patient may call his primary care provider (PCP) at step 1608 and then find that the symptoms were not serious and that he is OK (step 1610). Alternatively, the call to the PCP may result in the patient going to the emergency room (step 1612) and being admitted to the hospital (1614). The patient may be discharged (step 1615) and provided a patch to wear (1630) for continuous monitoring following emergency room discharge. Alternatively, admission to the hospital (step 1614) may result in a cardiologist referring the patient to an electrophysiologist (EP) (step 1622). The EP may place the patch on the patient (step 1624) an initiate continuous monitoring.

Another result of the patient call to the PCP (step 1608) is that the PCP will mail or otherwise provide a patch to the patient with instructions to affix the patch and initiate continuous monitoring (step 1618). Another alternative is that the patient will have an office visit with the PCP (step 1616). The visit may result in a patch being mailed to the patient (step 1618) or being applied to the patient by the PCP (step 1628) in the PCP office. Another option is that the PCP will refer the patient to a cardiologist (step 1620) who applies the patch to the patient (step 1626).

At the conclusion of any of the above treatment scenarios, there is a patch on the patient (step 1630).

Once the patch is associated with a specific patient, a number of various steps may be undertaken depending upon the specific circumstances of the patient and the desired treatment plan desired by a physician. In addition to the steps detailed below, the patch may operate as described above with regard to embodiments of the cardiac monitor 100 to record all cardiac activity during a monitoring period. The patch may be used to record everything without any assessment (step 1632) during the monitoring period. Alternatively, the patient may call his physician if symptoms are perceived. General parameters are used to trigger recording (passive) (step 1634). Events or symptoms felt or noted by a patient may also be recorded (step 1636) through activation of an event registration button. This triggering does not impede or alter the storage of the continuously recorded cardiac data, but rather adds a notation to alert a physician analyzing the data subsequently after monitoring has been completed that the patient felt an event or symptom at this point of the continuous data recording. A patient may be provided with multiple kinds of patches (step 1638). The patient may be provided with a standard patch (same hardware and construction) that undergoes software programming in the physician's office (step 1640). At the end of the monitoring period, continuous cardiac data has been collected (1642). Detecting an ECG signal of a mammal and storing all the detected ECG signals are performed without identifying ECG events in the information collected during the monitoring period.

Since the monitoring period is a pre-determined period, notification of the conclusion of monitoring may be performed in any number of ways. A notification may be provided to the patient to mail the patch in for processing (step 1644). The patient may receive a call from a nurse or other health care provider (step 1646). The patient may simply go to a pre-arranged appointment where the patch is removed (step 1648). An automated calling program may notify the patient that monitoring has ended (step 1650). The patient may receive a notice in the mail with a reminder of the monitoring end point and also include instructions on how to return the device (step 1652). The patient may be notified of the conclusion of monitoring via a wireless messaging system (1654). An audible alarm or beep may be emitted to indicate the end of monitoring (step 1656). Optionally, the notification may be from a configuration of lights on the monitor as described above with regard to FIG. 6C.

Once monitoring has ended, the device may be returned for processing in any of a number of ways. The device may returned to the hospital which will then forward the device and/or data on for processing (step 1658). The device may be picked up from the patient (step 1650). The patient may also mail the patch themselves to a processing center or health care provider (step 1662). The patch may include a design that allows it to unfold into a larger shape to make handling easier (step 1664). Optionally, the patch may be returned using an envelope (step 1666), by affixing it to a postcard (step 1668), by using a return mailer from a monitoring company or health care provider (step 1670) or by using a card in a wallet (step 1672). Once the patch has been removed from the patient, it is provided to, delivered to or made available to the monitoring company using any of the techniques above (step 1674). After the monitoring company has the patch, it will be able to retrieve stored information related to substantially all detected cardiac signals from the monitor. Next, the data is analyzed or processed (step 1676). This analyzing step is performed after the ECG monitor is removed from the mammal. The retrieved information from the patch is analyzed to identify ECG events. Additionally, the algorithms may be used to process stored information to determine the presence of an arrhythmia. Additionally, there is also the step of processing information stored on the device using more than one algorithm to determine the presence of an arrhythmia.

After data processing, a generic report (step 1680) or a specific report may be generated. Additionally or alternatively, the output of data processing may be made available through a website (1678) where a user may select other techniques to process and evaluate the collected data. As a result of reviewing the report or using the website, or in any event, the monitoring company may provide additional details on request (step 1682).

At the conclusion of the monitoring process, a patient may return to his PCP for further evaluation and diagnosis (step 1684). As a result of the evaluation of the monitoring process, the PCP may refer the patient to a cardiologist (step 1686), apply a new patch to the patient and initiate an additional monitoring session (step 1688) or determine that the patient is OK and requires no further treatment or monitoring (step 1690).

Figure 17:
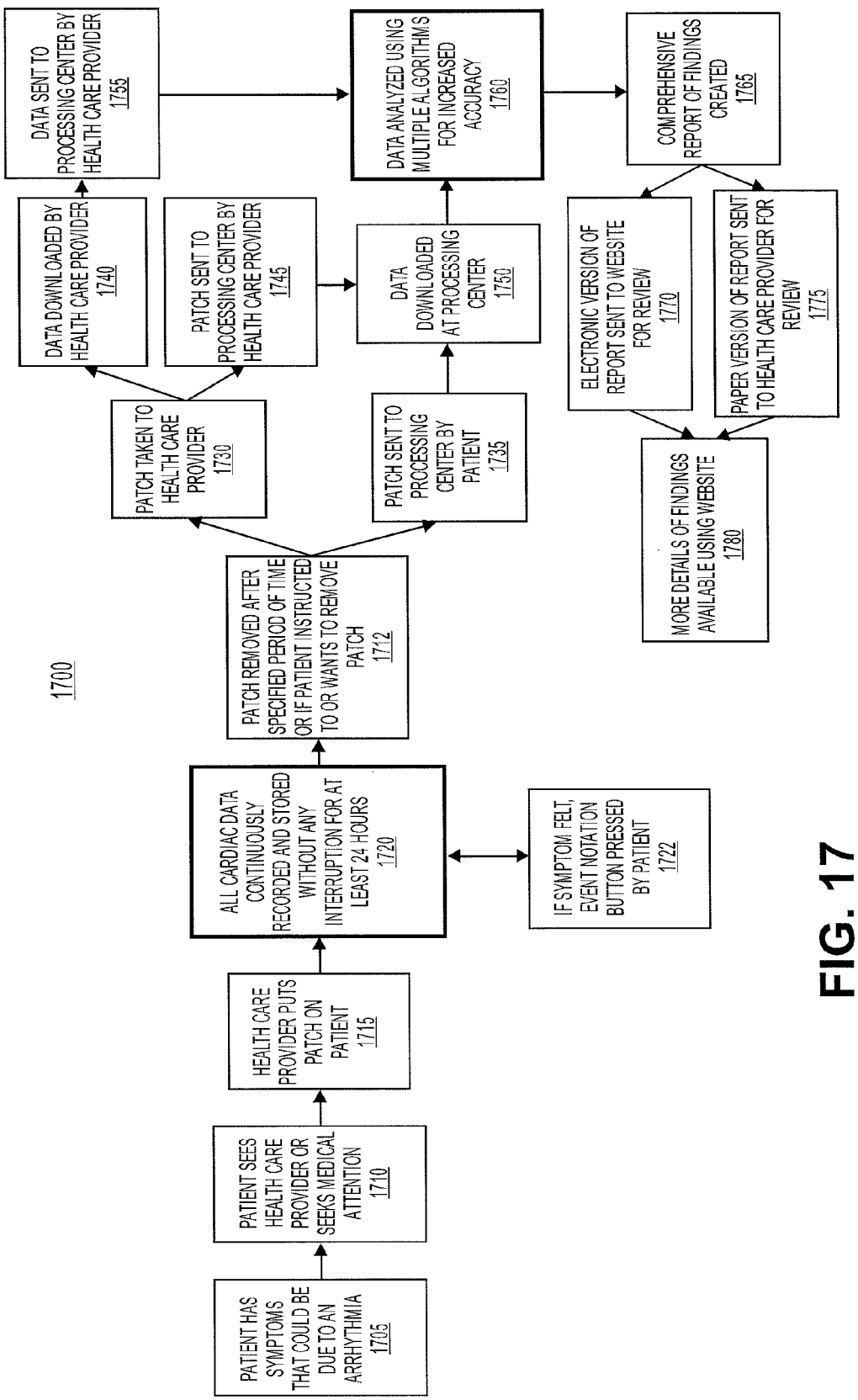
FIG. 17 illustrates an alternative cardiac data processing method based on the availability of continuous cardiac data.

Turning now to FIG. 17, another alternative cardiac data processing method 1700 that is enabled because of the availability of continuous cardiac data provided by embodiments of the continuous cardiac monitor 100 is shown.

A patient has symptoms that could be due to an arrhythmia (step 1705). Next, the patient sees a health care provider or seeks medical attention (step 1710). The health care provider puts a patch on the patient (step 1715) and initiates the monitoring period. All cardiac data is continuously recorded and stored without any interruption for at least 7 days (step 1720). During the monitoring period, if a symptom is felt, the event registration button is pressed by patient (step 1722).

The patch is removed after a specified period of time or if the patient is instructed to or wants to remove the patch (step 1725).

Next, the patch may be taken to the health care provider (step 1730) or can be sent to the processing center by patient (step 1735). If the patch is taken back to the health care provider, the data may be downloaded by the health care provider (step 1740). The patch can also be sent to the processing center by the health care provider (step 1745) or the patient (step 1735), and the data is downloaded at the processing center (step 1750).

Whether the data is sent to the processing center by the health care provider (step 1755) or downloaded by the processing center (step 1750), the continuous cardiac data obtained during the monitoring period is analyzed using multiple algorithms for increased accuracy (step 1760). Thereafter, a comprehensive report of findings is created (step 1765). An electronic version of the report may be sent to a website for review (step 1770). Optionally, a paper version of report can be sent to a health care provider for review (step 1775). Regardless of how the results of the comprehensive findings are provided, more details of the findings are available using the website (step 1780).

Additional other methods are enabled by the embodiments of the continuous cardiac monitors described herein. FIG. 18 illustrates one method of storing all or substantially all of the cardiac data of a mammal as illustrated by method 1800. In this method of obtaining cardiac information from a mammal, the first step is attaching a self-contained, wearable, portable cardiac monitor to the mammal to create a chamber containing electrodes used to detect cardiac signals from the mammal (step 1810). Next, using the self-contained, wearable, portable cardiac monitor, continuously detect without analyzing the cardiac signals from the mammal for at least 24 hours (step 1820). Finally, store information related to substantially all detected cardiac signals in the cardiac monitor (step 1830). In one aspect of this method, the self-contained, wearable, portable cardiac monitor comprises: a plurality of electrodes, a power source and memory contained within a watertight housing. Alternatively, the cardiac monitor may provide a mammal perceivable indication that the cardiac monitor is operating. In another aspect of operation, the cardiac monitor provides an indication that the cardiac monitor is operating after the attaching step. The operation of the cardiac monitor based on this indication shows that continuous cardiac data is being collected by the cardiac monitor.

The steps detailed in method 1800 may also be modified in certain embodiments. For example, the detecting and storing steps are performed without identifying cardiac events in the information related to substantially all detected cardiac signals. In another alternative, the detecting and storing steps are performed without transferring information between the housing and a device not attached to the mammal. In another alternative, the detecting and storing steps are performed without transferring information between the housing and a device not contained within the housing.

The steps of the method may be performed in a certain order, as discussed above. Optionally, for example, the order may be changed or additional steps added. The providing step is performed after the attaching step, for example. In another example, the providing step is performed after the storing step. In another example, the providing step is continuously performed during a continuously detecting step. Optionally, the attaching step includes placing the electrodes on the mammal and sealing the electrodes between the housing and the mammal using an adhesive on a rim of the housing that surrounds the electrodes.

Other steps may be taken in addition to those detailed in method 1800. One step that may be added includes retrieving stored information related to substantially all detected cardiac signals from the monitor. Furthermore, the retrieved information to identify cardiac events may be analyzed. Optionally, the analyzing step is performed after the cardiac monitor is removed from the mammal. In another alternative, the cardiac monitor is removed from the mammal before the retrieving step. In another alternative, information from the storing step is processed to evaluate the presence of an arrhythmia during a time interval indicated by the mammal.

The method 1800 may also be modified to include different techniques for processing continuous cardiac data. For example, information from the storing step may be processed to determine the presence of an arrhythmia. Optionally, information from the storing step is processed using more than one algorithm to determine the presence of an arrhythmia. Alternatively, information from the storing step is processed to evaluate the presence of an arrhythmia during a selected time interval. In one embodiment, the information from the storing step is processed during the same selected time interval on more than one day.

The availability of self-contained, wearable, portable cardiac monitors such as those embodiments described above, enable new processes of analyzing continuously collected cardiac data. One exemplary process 1900 of collecting and analyzing cardiac data is illustrated in FIG. 19. The first step in this process of analyzing cardiac information is to collect a plurality of self-contained, wearable, portable cardiac monitors, each of the cardiac monitors electronically storing at least 24 hours of continuously detected and unanalyzed cardiac signals from a mammal (step 1910). This step is possible using any of the embodiments of the continuous cardiac monitor 100 described above. The next step, step 1920, involves retrieving cardiac information stored in each of the plurality of self-contained portable cardiac monitors. Finally, at step 1930, retrieved cardiac information is forwarded. Forwarded in the context of this application includes physically forwarded such as when a hardcopy of the data is provided to a user. Forwarding also includes activity that purposely provides information to a user such as in a letter, an e-mail or other form of communication to a user. Forwarding also includes the act of making the retrieved data available for access by a user. In this context, retrieved data would be considered forwarded when the data is available for access by a user on a website, dedicated program or by other means accessible to the user by user access.

The specific details of the method 1900 may be modified. For example, in one alternative, the mammal specific information in at least one of the plurality of self-contained, wearable, portable cardiac monitors includes substantially all of the cardiac information from a mammal for at least 7 days. In another alternative, the cardiac information in the forwarding step includes substantially all of the cardiac information from a mammal for at least 7 days. In yet another alternative, the forwarding step includes providing mammal specific cardiac information to a physician identified in the collecting step.

The specific steps of the method 1900 may also be modified. For example, the method 1900 may include the step of sending the collected self-contained portable cardiac monitors to a processing center before the retrieving step. In one specific embodiment, the forwarding step includes the step of electronically sending retrieved cardiac information to a processing center. In another alternative, the step of removing a self contained portable cardiac monitor from a mammal is performed before the collecting step.

The process 1900 may also be modified to include a variety of alternative processing steps. In one alternative, the retrieved cardiac information may be analyzed to identify cardiac events or parameters. Optionally, the analyzing step is done after the forwarding step. In another step, information from the forwarding step is processed to determine the presence of an arrhythmia. In another alternative, the information from the forwarding step may be processed using more than one algorithm to determine the presence of an arrhythmia. In another additional step, the information from the forwarding step may be processed to evaluate the presence of an arrhythmia during a selected time interval. The selected time interval may be during the same selected time interval on more than one day or a time interval indicated by the mammal. In another step of the process, information from the forwarding step may be processed to determine the presence of an arrhythmia.

The method 1900 may also be modified in other ways, such as to provide a user access to data collected by the continuous cardiac monitor. One additional step includes providing a user access to information from the retrieving step or the forwarding step so that the user may process the provided information using more than one algorithm to determine the presence of an arrhythmia. Alternatively, another additional step provides a user access to information from the retrieving step or the forwarding step so that the user may process the provided information to evaluate the presence of an arrhythmia during a time interval indicated by the mammal. In yet another step, a user is provided access to information from the retrieving step or the forwarding step so that the user may process the provided information to evaluate the presence of an arrhythmia during a selected time interval. In one alternative, the provided information is processed during the same selected time interval on more than one day.

While numerous embodiments of the present invention have been shown and described herein, one of ordinary skill in the art will appreciate that such embodiments are provided by way of example only. Numerous variations, changes, and substitutions will now occur to those skilled in the art without departing from the invention. It should be understood that various alternatives to these embodiments of the invention described herein may be employed in practicing the invention. It is intended at the following claims defined the scope of the invention and it methods and structures within the scope of these claims and their equivalents be covered thereby.

What is claimed is:

1. A method of analyzing cardiac rhythm information, the method comprising:
    collecting a plurality of self-contained, wearable, portable cardiac monitors, each of the cardiac monitors removed from a different mammal after having been worn by each mammal continuously without removal for at least 24 hours, and each of the cardiac monitors including at least two electrodes, an action sequencer having no central processing unit for rhythm analysis, and a memory containing at least 24 hours of continuously detected, stored and unanalyzed cardiac rhythm information, comprising both normal cardiac rhythm information and abnormal cardiac rhythm information collected from the mammal, wherein each cardiac monitor includes a watertight housing enclosing at least the action sequencer and the memory electronically coupled with the electrodes;
    opening the watertight housing on each cardiac monitor to retrieve the at least 24 hours of continuously detected, stored cardiac rhythm information stored in each of the collected plurality of self-contained portable cardiac monitors;
    analyzing, after the retrieving step, the at least 24 hours of continuously detected, stored cardiac rhythm information to generate a report; and
    providing the report to a user.

2. The method of analyzing cardiac rhythm information according to claim 1, wherein the analyzing step comprises electronically sending the retrieved cardiac rhythm information to a processing center.

3. The method of analyzing cardiac rhythm information according to claim 1, wherein the analyzing step comprises analyzing the at least 24 hours of continuously detected, stored cardiac rhythm information to identify cardiac events or parameters.

4. The method of analyzing cardiac rhythm information according to claim 1, wherein at least a majority of the plurality of self-contained, wearable, portable cardiac monitors includes substantially all of the continuously detected, stored cardiac rhythm information from a mammal for at least 7 days.

5. The method of analyzing cardiac rhythm information according to claim 1, wherein the retrieved cardiac rhythm information includes substantially all of the cardiac rhythm information from a mammal for at least 7 days.

6. The method of analyzing cardiac rhythm information according to claim 1, wherein the providing step includes providing retrieved cardiac rhythm information to a physician identified in the collecting step.

7. The method according to claim 1, wherein the analyzing step comprises analyzing the at least 24 hours of continuously detected, stored cardiac rhythm information to determine the presence of an arrhythmia.

8. The method according to claim 7, wherein analyzing comprises using more than one algorithm to determine the presence of the arrhythmia.

9. The method according to claim 1, wherein the analyzing step comprises analyzing the at least 24 hours of continuously detected, stored cardiac rhythm information to evaluate the presence of an arrhythmia during a selected time interval.

10. The method according to claim 9, wherein the cardiac rhythm information is processed during the same selected time interval on more than one day.

11. The method according to claim 1, wherein the analyzing step comprises analyzing the at least 24 hours of continuously detected, stored cardiac rhythm information to evaluate the presence of an arrhythmia during a time interval indicated by the mammal.

12. The method according to claim 1, wherein the analyzing step comprises providing the at least 24 hours of continuously detected, stored cardiac rhythm information to a user so that the user may process the provided information using more than one algorithm to determine the presence of an arrhythmia.

13. The method according to claim 1, wherein the analyzing step comprises providing the at least 24 hours of continuously detected, stored cardiac rhythm information to a user so that the user may process the provided information to evaluate the presence of an arrhythmia during a selected time interval.

14. The method according to claim 13 wherein the provided information is processed during the same selected time interval on more than one day.

15. The method according to claim 1, wherein the analyzing step comprises providing the at least 24 hours of continuously detected, stored cardiac rhythm information to a third party so that the third party may process the provided information to evaluate the presence of an arrhythmia during a time interval indicated by the mammal prior to the collecting step.

* * * * *